(12) United States Patent
Berrang et al.

(10) Patent No.: US 7,951,063 B2
(45) Date of Patent: May 31, 2011

(54) TOTALLY IMPLANTABLE HEARING PROSTHESIS

(75) Inventors: Peter Berrang, Saanichton (CA); Terence Miranda, Cobble Hill (CA); Alan Lupin, Victoria (CA); Ian Booth, Victoria (CA)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 12/236,746

(22) Filed: Sep. 24, 2008

(65) Prior Publication Data

US 2009/0030529 A1    Jan. 29, 2009

Related U.S. Application Data

(62) Division of application No. 10/624,467, filed on Jul. 23, 2003, now Pat. No. 7,442,164.

(51) Int. Cl.
*H04R 25/00* (2006.01)
(52) U.S. Cl. .......................................... 600/25
(58) Field of Classification Search .................. 600/25; 623/10; 607/57, 137; 381/312
See application file for complete search history.

(56) References Cited

U.S. PATENT DOCUMENTS

| | | | |
|---|---|---|---|
| 5,277,694 A | 1/1994 | Leysieffer et al. | |
| 5,360,388 A | 11/1994 | Spindel et al. | |
| 5,498,226 A | 3/1996 | Lenkauskas | |
| 5,772,575 A | 6/1998 | Lesinski et al. | |
| 5,800,336 A | 9/1998 | Ball et al. | |
| 5,906,635 A | 5/1999 | Maniglia | |
| 6,217,508 B1 * | 4/2001 | Ball et al. | ......................... 600/25 |
| 6,251,062 B1 | 6/2001 | Leysieffer | |
| 6,272,382 B1 | 8/2001 | Faltys et al. | |
| 6,308,101 B1 | 10/2001 | Faltys et al. | |
| 6,358,281 B1 | 3/2002 | Berrang et al. | |
| 2002/0019669 A1 | 2/2002 | Berrang et al. | |
| 2002/0076071 A1 * | 6/2002 | Single | ........................... 381/312 |
| 2003/0055311 A1 * | 3/2003 | Neukermans et al. | ........... 600/25 |

FOREIGN PATENT DOCUMENTS

WO    01/93635    6/2001

OTHER PUBLICATIONS

Hakansson et al., "Ten Years of Experience With the Swedish Bone-Anchored Hearing System" Annals of Otology, Rhinology & Laryngology, Oct. 1990, vol. 99, No. 10, Part 2.
Stenfeldt, Hearing by Bone Conduction Physical and Physiological Aspects, web printout from Chalmers University of Technology, 1999.

* cited by examiner

*Primary Examiner* — Charles A Marmor, II
*Assistant Examiner* — Christine D Hopkins
(74) *Attorney, Agent, or Firm* — Sunstein Kann Murphy & Timbers LLP

(57) ABSTRACT

The invention comprises a totally implantable hearing prosthesis for hearing impaired persons. An inertial vibrational element is hermetically sealed and implanted in bone between the lateral and superior semicircular canals without breaching the integrity of the canals. The vibrational element is adapted to vibrate the walls of the canals and the fluids contained therein, thereby vibrating contiguous fluids within the cochlea thus stimulating hair cells and creating a hearing percept. The invention can also be adapted to be a tinnitus masking system, and/or used in combination with a cochlear implant hearing system.

4 Claims, 18 Drawing Sheets

TOTALLY IMPLANTABLE HEARING PROSTHESIS

The present Application is a Divisional of U.S. patent application Ser. No. 10/624,467, filed Jul. 23, 2003, now U.S. Pat. No. 7,442,164, the entire disclosure of which is herein incorporated by reference in its entirety.

FIELD OF THE INVENTION

This invention relates to an implantable prosthesis for use in a hearing system to treat hearing loss, tinnitus, or a combination of hearing loss and tinnitus.

BACKGROUND OF THE INVENTION

Hearing loss affects over 10% of the North American population, with over 8% of this group suffering from profound deafness. Tinnitus, described as "hissing, roaring or ringing" in the ear(s) or head, is an auditory perception not produced by an external sound. In the US, as many as 50 million people are affected by tinnitus to some degree and up to 12 million have sought medical attention for the problem. About 1 million sufferers are so seriously debilitated that they cannot function on a normal, day-to-day basis.

Hearing aids, cochlear implants, and tinnitus maskers can be used to help individuals with mild to severe hearing loss, severe to profound deafness, and tinnitus, respectively. By amplifying environmental sounds, hearing aids and cochlear implants often serve the dual purpose of providing a hearing percept and masking tinnitus, for those who suffer from both conditions. A tinnitus instrument refers to a hearing aid that also provides an overlying masking noise. Tinnitus instruments are used for hearing impaired tinnitus sufferers who do not obtain sufficient tinnitus relief from the amplification of environmental sounds alone.

The aforementioned devices used to treat hearing loss and/or tinnitus can be worn, at least in part, externally on the body in the area of the ear. As a result, these devices can stigmatize the wearer and therefore lead to device rejection. For example, the penetration rate of hearing aids in the US is only about 20% due, in part, to patient-related limitations such as stigma and vanity (Sweetow, R. W., "An Analysis of Entry-Level, Disposable, Instant-Fit and Implantable Hearing Aids", *The Hearing Journal,* 54(2), 2001).

Various prior art describes partially or fully implantable devices that induce a hearing percept via bone conduction. The US FDA-approved bone-anchored hearing aid (BAHA), as described by Hakansson et al. in "Ten Years of Experience with the Swedish Bone-Anchored Hearing System", Supplement 151, 99(10) Part 2:1-16, 1990, consists of a titanium screw, secured in temporal bone, and attached percutaneously to a vibrating sound processor. The BAHA, which is a commercial device sold by Entific Medical Systems of Sweden, is indicated for people with conductive or mixed hearing losses, with a bone-conducted pure-tone average of less than 60 dB HL. Although it is reported that the BAHA provides a satisfactory percept in appropriately selected patients (e.g., Lustig et al., "Hearing Rehabilitation Using the BAHA Bone-Anchored Hearing Aid: Results in 40 Patients", *Otology and Neurotology* 22:328-34, 2001), it has the significant disadvantages of poor aesthetics and infection/inflammation around the implantation site. Additionally, U.S. Pat. Nos. 4,498,461; 4,612,915; and 4,904,233 describe a particular type of coupling to a bone-anchored hearing aid. In his PhD thesis, Stenfeldt describes implanting a bone-anchored hearing aid closer to the cochlea by implanting it within the mastoid bone and attaching it to a microphone either implanted in the ear canal or housed in an external unit (Stenfeldt, S. "Hearing by Bone Conduction, Physical and Physiological Aspects", Technical Report No. 358, School of Electrical and Computer Engineering, Chalmers University of Technology, Goteborg, 1999). The exact position of the bone conducting device is not specified. Stenfeldt's proposed setup also mentions an implanted rechargeable battery and electronics package and an internal coil for recharging purposes. He further mentions a similar unit, but without an implanted microphone, to be used as a totally implanted tinnitus masker. Stenfeldt's thesis provides very limited information about the implanted bone conductor; he does not provide any engineering designs, calculations, or suggestions as to how such devices could be fabricated PCT patent WO 01/93635 A1 describes a hearing aid device of the bone conduction type that is comprised of an implantable part (vibrator) osseointegrated partly inside the skull bone, and an external part (microphone, electronic circuitry, power source). The WO 01/93635 device comprises an external and an implantable component such that the device as a whole is not entirely implantable. The vibrator of the WO 01/93635 patent is located partly outside the skull bone and at the side of the head. The WO 01/93635 device is also preferably electromagnetic and is therefore incompatible with magnetic resonance imaging (MRI).

There exists prior art that describes partially or fully implantable hearing aids that place a vibrating prosthesis on the ossicular chain in order to transmit vibrations to the cochlea. For example, U.S. Pat. No. 5,800,336, issued to Ball, et al. discloses a "floating mass transducer", consisting of an electromagnet attached to bone within the middle ear, that delivers amplified vibrations to the inner ear. Furthermore, in U.S. Pat. No. 5,800,336, Ball, et al. note that the properties of piezoelectrics and bimorph piezoelectrics can provide a basis for floating mass transducers.

In U.S. Pat. No. 5,558,618, Maniglia describes a semi-implantable middle ear hearing device that consists of a magnet mounted to the ossicular chain that is driven by an implanted electromagnetic driving coil. Dormer, in U.S. Pat. No. 6,277,148, describes a middle ear magnet implant driven by a coil placed in the external auditory canal.

There also exists prior art that describes partially or fully implantable hearing aids that place a vibrating prosthesis directly on the otic capsule. For example, in U.S. Pat. No. 5,360,388, Spindel et al. describe an implantable hearing aid that includes an electromagnet fixed to the round window of the cochlea. In U.S. Pat. No. 5,277,694, Leysieffer, et al. describe a vibrating piezoelectric device for direct mechanical stimulation of the middle or inner ear. In U.S. Pat. No. 5,772,575, Lesinski et al. describe a fully implantable hearing aid, suitable for conductive and/or sensorineural hearing loss, that uses a piezoelectric transducer implanted adjacent to the oval window of the inner ear. In U.S. Pat. No. 5,879,283, Adams et al. describe a method and apparatus for improving the frequency response of a piezoelectric transducer in an implantable hearing system. The improvements are achieved by using different numbers of transducer elements and/or transducers of different dimensions and/or different material properties and then mounting these transducers, using different mounting techniques, to different auditory elements (e.g., ossicles, inner ear).

Most of the prior art describing fully implantable hearing aids and/or tinnitus maskers (e.g., U.S. Pat. Nos. 5,800,336; 5,558,618; 6,277,148; 5,360,388; 5,277,694; 5,772,575) have the fundamental and serious disadvantage that the surgery required for implantation of the electromechanical transducer requires mechanical manipulations on the ossicular chain or directly at the entry area of the inner ear (oval or round window) and thus involves considerable risk of middle or inner ear impairment. Furthermore, the necessary surgical opening of a sufficiently large access to the middle ear from the mastoid can involve the serious risk of facial nerve damage and the associated partial paralysis of the face. Moreover, it cannot be guaranteed that the mechanical coupling will be of a long term, stable nature or that additional clinical damage will not occur (e.g., pressure necroses in the area of the ossicles).

Various prior art attempts to circumvent some of the aforementioned disadvantages of implantable hearing aids/tinnitus maskers. In U.S. Pat. No. 5,498,226, Lenkauskas describes a totally implanted hearing device placed in the mastoid area that transfers vibrations to the cochlea, via the perilymph, by drilling a hole into the posterior semicircular canal (i.e. a fenestration), covering such hole with perichondrium or fascie, and placing a piston over the fenestration, thereby bypassing the middle ear system. Possible surgical complications of this procedure include excessive leakage of perilymph fluid, rupture of the membranous labyrinth, and serious infection of inner ear fluids. Furthermore, Lempert, J. "Fenestra Non-Ovalis: A New Oval Window for the Improvement of Hearing in Cases of Otosclerosis", Archives of Otolaryngology, 34:880-912, 1941, describes a tendency for bone to repair itself after injury, wherein a significant percentage of fenestrated horizontal semicircular canals (i.e. 88 of 300) closed due to either bone regeneration or the formation of fibrous connective tissue. Accordingly, such bone growth will increase the stiffness of the covering over the trauma site of the fenestration, thereby attenuating the action of the vibrating piston as described in U.S. Pat. No. 5,498,226. U.S. Pat. No. 6,251,062, which describes an implantable device for treatment of tinnitus, avoids entering the middle or inner ear spaces by positioning an electroacoustic transducer in the mastoid cavity. In at least one embodiment, sound emitted from the transducer travels via the natural passage of the aditus ad antrum from the mastoid to the tympanic cavity in the area of the middle ear. This sound causes mechanical vibrations of the eardrum which travel via the mechanical transmission through the middle ear ossicles to the inner ear or via direct acoustic excitation of the oval or round window of the inner ear. U.S. Pat. No. 6,251,062 suffers from the same disadvantage as other implantable hearing aids/tinnitus maskers in that it relies on the middle ear space for transmission of sound to the inner ear. Therefore, the device(s) may not be indicated for use in patients who have non-treatable or transient middle ear pathology (e.g., otosclerosis, middle ear fluid), congenital malformations (e.g., atresia, malformed/missing ossicles) or who have had surgery affecting the mastoid or middle ear space (e.g., radical mastoidectomy).

There exists prior art describing fully implantable cochlear prostheses, for example, see U.S. Pat. No. 6,358,281 B1 and US Patent Application 2002/0019669 A1, included herein by reference, and U.S. Pat. Nos. 5,906,635; 6,272,382 B1 and 6,308,101 B1. Such prostheses are devices that stimulate the auditory nerve and are indicated for profoundly hearing impaired individuals who obtain inadequate benefit from the use of hearing aids. There is a significant number of severely hearing impaired individuals who show relatively good preservation of low frequency hearing and little or no functional hearing in the high frequency range above 1 kHz. Even with optimal acoustic amplification, speech understanding often remains very poor (monosyllabic understanding <30-40%) for these individuals. Recent data indicate that, for individuals with sufficient low-frequency hearing, the combination of acoustic and electric stimulation (in the same ear) provides additional benefit for speech understanding in comparison to electric stimulation via cochlear implantation alone (see e.g. Tillein et al., "Simultaneous Electrical and Acoustical Stimulation of the Normal Hearing Ear. Results from Acute and Chronic Experiments with Cats and Guinea Pigs", Oral Presentation, 2001 Conference on Implantable Auditory Prostheses, Aug. 19-24, 2001; Kiefer et al., "Combined Electric-Acoustic Stimulation of the Auditory System—Results of an Ongoing Clinical Study", Oral Presentation, 2001 Conference on Implantable Auditory Prostheses, Aug. 19-24, 2001; McDermott et al., "Combining Electric and Acoustic Hearing: Perceptual Characteristics and Improved Sound Processing", Oral Presentation, 2001 Conference on Implantable Auditory Prostheses, Aug. 19-24, 2001; Turner & Gantz, "Combining Acoustic and Electric Hearing for Patients with high-Frequency Hearing Loss", Oral Presentation, 2001 Conference on Implantable Auditory Prostheses, Aug. 19-24, 2001). Acoustic stimulation is typically provided to such cochlear implant recipients through the use of an acoustic hearing aid.

The prior art, describing cochlear prostheses, does not appear to allow for a totally implanted hearing aid in addition to the totally implanted cochlear prosthesis. Thus, the advantage of total implantation would be significantly diminished for those cochlear implant recipients who would benefit from the additional use of externally worn acoustic hearing aid(s).

Thus, there is need for a totally implantable, low power consuming, vibrational element (i.e. a mechanical transducer) that can provide stimulation to the cochlea. Such a transducer must be easily and safely implanted into nearly all individuals. Additionally, the surgery should be fully reversible and cause no permanent side effects. Ideally, the transducer would not rely on transmission through the middle ear space and therefore could be used for individuals with (or without) middle ear pathology. The transducer should have enough vibrational capacity to ameliorate severe hearing loss across the speech frequency range yet be flexible enough to provide sub-threshold levels of stimulation or stimulation in selected frequency regions only. The transducer could then be used as an integral part of a fully (or partially) implantable hearing aid, tinnitus masker, or tinnitus instrument. Another potential use for the transducer is in combination with a fully implantable cochlear implant for those cochlear implant candidates who gain greatest benefit from electric plus acoustic stimulation (e.g., those with severe progressive hearing loss or those who have substantial low frequency hearing but a profound loss in the higher frequencies). The transducer would provide acoustic stimulation in the frequency range where there is residual aidable hearing.

SUMMARY OF THE INVENTION

In one of its aspects, the invention comprises a hearing device that includes a vibrational assembly within a housing that is implantable with the bone near the semicircular canals.

The assembly generates vibration that is transmitted through the housing and the bone and is perceived by the subject as sound.

In another aspect of the invention, the vibrational assembly includes a controllable vibrating element, and an inertial mass that vibrates in response to vibration of the vibrating element.

The preferred embodiment of the present invention provides for a hermetic, biocompatible, totally implantable hearing device, adapted to function as a hearing aid and/or tinnitus instrument. The preferred embodiment comprises an inertially driven vibrational assembly enclosed in a hermetic housing and adapted to be implanted in bone near the semicircular canals, a microphone, a hermetic housing containing control electronics and/or a battery, a coil for receiving and/or sending data and/or power transcutaneously and an alignment magnet contained within the coil.

An aspect of the invention is the vibrator (or transducer), which vibrator has been adapted to be relatively easy and safe to implant, is totally implantable, is explantable, osseointegrates to surrounding bone, causes no permanent side effects, has low power consumption, and does not rely on transmission through the middle ear space. The vibrator, which consists of a vibrational assembly enclosed within a biocompatible housing, is preferably implanted within bone between the lateral and superior semicircular canals of the otic capsule. Such close placement of the vibrator to the lateral and/or superior semicircular canals will allow high power, high fidelity vibrations to pass from the vibrator, through the semicircular canals, and via endolymph and perilymph fluids contained therein, to the basilar membrane and the hair cells in the cochlea. Clinical results from the fenestration operation (Lempert, J., "Improvement of Hearing in Cases of Otosclerosis" A New One-Stage Surgical Technique", Archives of Otolaryngology, 28:42-97, 1938) show that vibrations are easily passed to the transducing elements of the cochlea from this location. Minimizing losses during transmission helps to minimize the power consumption of the vibrator. Low power consumption is a key consideration in totally implantable devices.

Correct intercanalicular placement of the vibrator ensures a safe, quick, reversible and relatively atraumatic surgery; it avoids mechanical manipulations and mass loading of the ossicular chain or entry into the middle or inner ear, thereby assuring that these structures are not damaged. Because intercanalicular placement avoids accessing the middle ear space, the risk of damage to the facial nerve is greatly reduced. Intercanalicular placement of the vibrator greatly reduces the risk that surgery or subsequent functioning of the vibrator, even in the long-term, will cause additional hearing loss, either conductive or sensorineural. Implantees can be reasonably assured that, if for some reason they do not want to use the device after surgery, they can turn off the device and use their previous hearing aid as before. Neither the surgery, nor the functioning of the vibrator, will cause any permanent changes to their auditory system. An additional advantage to placing the vibrator in the intercanalicular space, as compared to other potential implantation sites close to the otic capsule, is that there is a relatively large amount of bone that can be excavated to place a relatively large transducer. Investigations have shown that a cylinder about 4.5 mm in diameter and about 3.5 mm in height can easily be placed in this location. Grooves on a portion of the outside walls of the vibrator help to osseointegrate it into the bone surrounding the otic capsule, and a silicone coating over the base and the basal part of the outside wall helps to focus vibrational energy preferentially towards the semicircular canals. Importantly, the vibrator does not breach the bony walls of the semicircular canals, thereby making surgical installation relatively simple and safe.

The vibrator can be incorporated into an implantable hearing aid, as well as other configurations such as: (a) a tinnitus masker and hearing aid combined, (b) a tinnitus masker only, and (c) a hearing device used in conjunction with a cochlear implant. The systems and instruments can be either partially, or totally implanted.

The vibrator may be operatively connected to a totally implantable hearing aid system comprised of a housing, microphone and RF coil. One embodiment of such other components is described in commonly owned U.S. Pat. No. 6,358,281 B1 and U.S. patent application Ser. Nos. 09/975,970 and 09/499,376 incorporated herein by reference. In the preferred embodiment, the implanted microphone receives and converts acoustic input to an electric current. Wires send these signals to a subcutaneous housing located under skin in the post-auricular area, which housing contains an on-off switch, a battery and various control electronics. Signals from the housing are then sent, via wires, to the vibrator located in the intercanalicular space. The vibrator then vibrates with sufficient force, across the speech frequency range, to ameliorate hearing loss up to and including the severe range. A subcutaneous RF coil, operatively connected to the housing, can be used to transcutaneously charge the battery within the housing, and communicate with electronics therein so as to adjust various functions and parameters to optimize hearing percepts by the implantee.

In an alternate embodiment, the vibrator is operatively connected to a totally implantable tinnitus masker. This embodiment comprises a vibrational assembly enclosed in a hermetic housing and adapted to be implanted in bone near the semicircular canals; at least one hermetic housing containing control electronics and/or battery; a coil for receiving and/or sending data and/or power transcutaneously; and an alignment magnet contained within the coil. Masking signals are generated in a subcutaneous housing located under skin in the post-auricular area, which housing contains an on-off switch, a battery and various control electronics. Masking signals generated from the housing are then sent, via wires, to the vibrator located in the intercanalicular space. A subcutaneous RF coil, operatively connected to the housing, can be used to transcutaneously charge the battery within the housing, and communicate with electronics therein so as to adjust various functions and parameters to optimize the masking signal delivered to the vibrator.

In another embodiment, the vibrator forms an integral part of a totally implantable tinnitus instrument. An implanted microphone receives and converts acoustic input to an electric current. Wires send these signals to a subcutaneous housing located under skin in the post-auricular area, which housing contains an on-off switch, a battery and various control electronics. Input received from the microphone are processed within the housing and mixed with masking signals generated within the housing. The combined signals are then sent, via wires, to the electromechanical transducer located in the intercanalicular space. A subcutaneous RF coil, operatively connected to the housing, can be used to transcutaneously charge the battery within the housing, and communicate with electronics therein so as to adjust various functions and parameters to optimize hearing percepts by the implantee.

In yet a further embodiment, the vibrator forms an integral part of a totally implantable cochlear implant, for example, as described in U.S. Pat. No. 6,358,281 B1 and US Patent Application 2002/0019669 A1, included herein by reference. This embodiment comprises a vibrational assembly enclosed in a hermetic housing and adapted to be implanted in bone near the semicircular canals; at least one microphone; at least one hermetic housing containing control electronics and/or battery; a coil for receiving and/or sending data and/or power transcutaneously and an alignment magnet contained within the coil; and at least one electrode array. In this embodiment, an implanted microphone, for example as described in U.S. patent application Ser. No. 09/499,376, included herein by reference, receives and converts acoustic input into electric current. Wires send these signals to a sound processing housing located under skin in the post-auricular area. The sound processor then filters the incoming signals. Low frequencies, for which there is residual aidable hearing, are converted into vibrations via the electromechanical transducer located in the intercanalicular space. High frequencies, for which there is no residual aidable hearing, are sent through the speech processor for conversion into electrical impulses. These impulses are then delivered to the spiral ganglion cells via an electrode array implanted into the cochlea. Only electrodes near the base of the cochlea need to be stimulated in order to transmit the high frequencies; this may allow for short electrode insertions.

The inertial mass or masses mounted in the vibrator may be mounted onto and/or between one or more vibrating elements. The hermetic vibrator housing is comprised of a biocompatible material, preferably titanium, or alloys thereof, and is substantially cylindrical in shape. The housing may contain one or more ridges and/or grooves that are radially or spirally disposed along one end of the outside cylindrical wall of the housing to help it securely osseointegrate within bony structure, preferably between the lateral and superior semicircular canals. The other end of the housing is coated with a substantially compliant material, such as silicone, to create an impedance mismatch between the coated housing area and surrounding bone.

The vibrator of this invention may use an inertial mass, driven by a stack of piezocrystals, encapsulated within a biocompatible hermetic housing. The vibrating piezoelectric elements may be substantially disk-shaped, stacked with alternating polarities, and separated by electrically conductive bonding layers, which serve to connect the elements mechanically and electrically. The electrically conductive bonding layers, preferably composed of one or more of gold, silver, tin, aluminum, indium or copper, extend beyond the outer circumference of the elements, thereby providing a contact pad for the attachment of wires, which serve to electrically connect the vibrating elements. The electrically conductive bonding layers can be joined by an electrically conductive link by bending an etched metal clip, preferably composed of one or more of gold, silver, tin, aluminum, indium or copper, to form the bonding layers and wire connecting alternating layers of the piezoelectric stack.

In an alternate embodiment of the vibrator of this invention, a vibrational assembly is enclosed in a hermetic housing, where the housing is adapted to be implanted in bone as part of a semi or fully implantable hearing device and where the top of the housing has been substantially adapted to be flexible. The vibrational assembly comprises an interconnected stack of piezoelectric crystals connected to the flexible housing top. Alternatively, the vibrational assembly comprises a piezoelectric bimorph element connected to the flexible housing top.

A yet further aspect of the invention is the interoperative attachment of a cable connected to the vibrator housing, wherein the base of the housing is connected to a plurality of electrically insulated lead-throughs disposed through the housing base. The cable carries electrical signals between the vibrator housing and a main housing containing batteries and electronics. The design of such interconnections, described in, for example, U.S. patent application Ser. No. 10/012,341 titled "Low Profile Subcutaneous Enclosure", included herein by reference, is non trivial.

Another aspect to this invention is the placement of the vibrator. The vibrational assembly is enclosed in a hermetic housing, which housing has been substantially adapted to be implanted in bone near the semicircular canals and/or cochlea, without breaching the canals or cochlea, as part of a semi or fully implantable hearing device. The vibrational assembly is adapted to vibrate the housing encasing the assembly, which housing vibrations are transmitted through surrounding structures to the cochlea thereby causing hearing percepts. The vibrator can be oriented such that the vibrational axis of motion is substantially perpendicular to the plane of the superior semicircular canal, with the base of the vibrator positioned away from the superior canal or it can be oriented such that the vibrational axis of motion is substantially perpendicular to the plane of the horizontal semicircular canal, with the base of the vibrator positioned away from the horizontal canal. Alternatively, the vibrator can be positioned in any orientation.

Another aspect to this invention is the implanted microphone. In the preferred embodiment, the microphone is enclosed in a hermetic housing and adapted to be implanted subcutaneously in bone and/or cartilage, substantially near the cymba concha of the auricle, as part of a semi or fully implantable hearing device. At least part of the housing encapsulating the microphone contains one or more circular and/or spiral grooves around its outside wall in order to aid osseointegration with the surrounding bone. Furthermore, at least part of the housing is coated with a compliant material, such as silicone, to increase the impedance to acoustic waves between the microphone housing and the surrounding bone and tissue.

An alternate embodiment of this invention is a semi or fully implantable hearing device, whose acoustic input mechanism comprises two or more microphones, each microphone enclosed in a hermetic housing, the housings adapted to be implanted subcutaneously in bone and/or cartilage. In one of the alternate embodiments, one or more microphones are adapted to be implanted, subcutaneously, in the posterior wall of the external auditory canal. In another embodiment, one or more microphones are adapted to be implanted, subcutaneously, at the side of the head, substantially behind and above the auricle. In another embodiment, one or more microphones are adapted to be implanted, subcutaneously, at the side of the head, substantially near the cymba concha of the auricle.

Yet a further aspect of the invention is the method of implantation of the hearing device in the desired location in the vicinity of the semicircular canals or vestibule. According to one embodiment, the invention is a surgical method, adapted to implant a vibrator substantially between and/or among the semicircular canals and/or vestibule without breaching said canals or vestibule, comprising the steps of forming an approximate two inch incision in the postauricular skin crease and exposing the surface of the mastoid bone, drilling through the mastoid until the antrum is found, thinning the posterior canal wall, identifying the horizontal canal and drilling out a cavity superior to it and recessing the cavity and packing the housing of said device into said cavity using bone paste so as to promote osseointegration.

In another aspect, the invention is a surgical method, adapted to implant an implantable microphone substantially within or near the cymba concha of the pinna, comprising the steps of approaching the cymba through a postauricular skin incision; raising the perichondrium on the medial side of the cymba, removing a circular core of cartilage from the auricular cartilage while not disturbing the lateral perichondrium, and inserting the implantable microphone and suturing the medial layer of perichondrium and the skin to cover the microphone and keep it in place.

The foregoing was intended as a broad summary only and of only some of the aspects of the invention. It was not intended to define the limits or requirements of the invention. Other aspects of the invention will be appreciated by reference to the detailed description of the preferred embodiment and to the claims.

BRIEF DESCRIPTION OF THE DRAWINGS

The preferred and alternative embodiments of the invention will be described by references to the accompanying drawings, in which.

DETAILED DESCRIPTION OF THE PREFERRED AND ALTERNATIVE EMBODIMENTS OF THE INVENTION

Figure 1A:
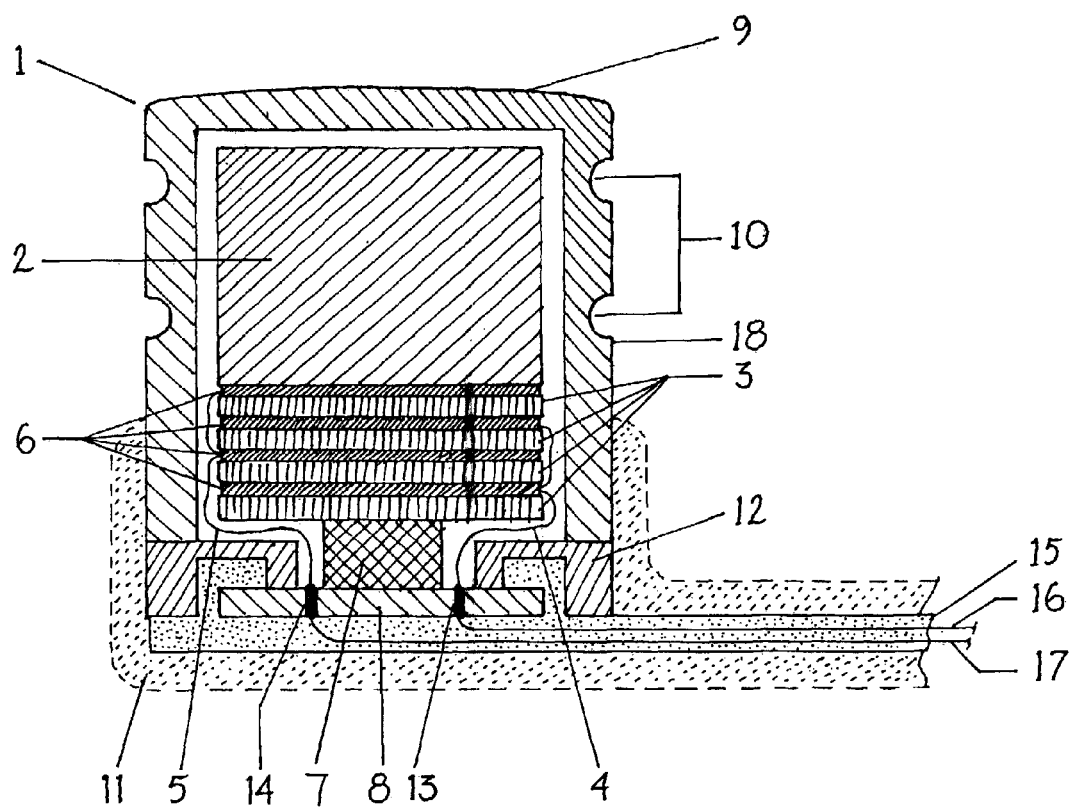
FIG. 1A shows a cross sectional view of the preferred embodiment of the inertial transducer encapsulated in a hermetic housing.

FIG. 1A shows a cross sectional view of the preferred embodiment of the hermetically sealed inertial mass vibrator 1. The transducer is comprised of a plurality of elements as follows: an inertial mass 2, a stack of piezoelectric elements 3 electrically connected together by wires 4 and 5, with a conductive bond layer 6 between the piezoelectric elements, an interface element 7 connecting the piezoelectric elements to a non-conductive insert 8, a hermetic housing 9 containing an osseointegration end with rings 10, an end coated with a compliant material 11, a base ring 12 with pins 13 and 14 penetrating a non-conductive insert 8 bonded to the base ring 12, with a bioinert cable 15 containing electrical conductors 16 and 17 electrically connected to pins 13 and 14.

The hermetic housing 9 is comprised of a bioinert material such as titanium, or alloys thereof, with substantially cylindrical walls 18, with one end sealed 9 and the other end coated with a compliant material 11. The diameter of the hermetic housing is about 2-6 mm, preferably about 4-5 mm. The length of the hermetic housing is about 2-5 mm, preferably about 3-4 mm. The thickness of the housing walls 18 is about 0.1-10.0 mm, preferably about 0.2-0.3 mm. The thickness of the sealed end 9 is about 0.1-1.0 mm, preferably about 0.2-0.3 mm.

The walls 18 of the sealed end of the hermetic housing 9 are adapted to be held firmly by bone surrounding the semicircular canals. The walls of such end contain one or more osseointegration rings 10, which can be radially or spirally disposed, and which aid the firm attachment of the hermetic housing within the bone around the semicircular canals (see also FIGS. 4 and 5), such attachment aiding the efficient transfer of vibrational energy from the sealed end of the hermetic housing 9 to the surrounding osseointegrated bone. The rings comprise one or more ridges and/or grooves in the walls penetrating to about half or less the wall thickness and having a width and depth of about 0.05-0.2 mm. The base end of hermetic housing 18, together with base ring 12 and cable 13, are coated with a compliant material 11, preferably silicone, or a silicone derivative material, which material acts as an impedance mismatched barrier to the transfer of vibrational energy from the end into bone surrounding such compliant material. An aspect of the present invention is to cause the sealed housing end 9 (held within the bony structure surrounding the semicircular canals) to vibrate, such vibrations passing through surrounding structures causing the fluids within the canals and cochlea to vibrate, thereby inducing hearing percepts to the implantee.

A base ring 12 comprising a bioinert material such as titanium is attached to one end of hermetic housing 18. Such attachment is achieved by laser welding, or other bonding means, to produce a hermetically sealed joint between the base ring 12 and the cylindrical housing 18. The outer diameter of the base ring is substantially similar to that of the hermetic housing 18. The base ring has an inner flange with inner diameter about 1-4 mm, preferably about 2-3 mm.

A non-conductive insert 8, is attached to the inner flange of base ring 12 using standard sealing methods well known to those skilled in the art. The insert is in the form of a disc made of electrically non-conductive, bioinert material such as alumina, with the diameter substantially larger than the inner diameter of the inner flange and smaller than the outer diameter of the base ring and hermetic housing. The insert is penetrated by electrical connector pins 13 and 14. Alternately, the insert 8 may be made of metal, such as titanium, wherein electrically isolated conductive pins 13 and 14 penetrate the insert.

Bioinert cable 15 is attached to the bottom of base ring 12 and insert 8. The cable is made of bioinert electrically non-conducting material such as the fluoropolymer FEP with two electrical conductors 16 and 17, preferably comprised of platinum, imbedded in the cable. The electrical conductors are insulated from the outside of the cable and from each other, and are attached to pins 13 and 14. Cable 15 can be bonded to the bottom of the base ring 12 and insert 8 using, for example, a bonding process as described in U.S. patent application Ser. No. 10/012,341, included herein by reference, so as to produce an ionic seal against surrounding body fluid or other medium external to the assembly, thereby preventing electrical conduction between pins 13 and 14.

In the preferred embodiment, illustrated in FIG. 1A, the walls of the sealed hermetic housing end 9 are caused to vibrate by causing inertial mass 2, constrained at one end, to vibrate. Inertial mass 2, is preferably comprised of a dense material, such as iridium, platinum, lead, rhenium, gold, or alloys thereof, with a mass of about 0.1-1.0 grams, preferably about 0.2-0.5 grams. Inertial mass 2 can be caused to vibrate over a frequency range of about 100-8000 Hz, preferably over the frequency range of about 200-6000 Hz, such frequency range being sufficient for the perception of audible speech. The vibration is in the piston mode; that is, the inertial mass moves alternately towards and away from the base ring 12. At no point in the vibrations does the inertial mass contact the inside end or inside walls of the hermetic housing.

The vibration is produced by impressing an alternating voltage on pins 13 and 14, such action causing piezoelectric elements 3 to alternately expand and contract at the frequency of the applied voltage. The total linear translation of piezoelectric elements 3 must be sufficiently large to induce a hearing intensity to the implantee of up to about 120 dB SPL equivalent. Such implantee-perceived hearing intensity requires the inertial mass to have a linear translation relative to the hermetic housing of about 0.1-10 microns, with the required linear translation generally decreasing with increasing frequency. To achieve such linear translation of the inertial mass 2 requires the sum of the piezoelectric elements 3 to expand and contract in thickness by an equal amount in response to the applied voltage. Preferably, piezoelectric elements 3 are comprised of one or more disc elements, each disc about 10-100 microns thick, polarized to expand or contract when a voltage is impressed across the faces of the disc. The piezoelectric elements are mechanically bonded together by electrically conductive bonding layers 6, with wires 4 and 5 connecting alternate bonding layers together and to pins 13 and 14. Those skilled in the art will recognize that there are many piezoelectric materials, such as PZT, PKM, barium titanate, and lead titanate zirconate, that expand or contract in the direction of an applied voltage, as illustrated by equation:

$$\rho T = d_{33} V$$

where $\rho T$ is the change in thickness of the piezoelectric material, $d_{33}$ is the piezoelectric strain coefficient, typically 100-1,000 picometers per volt, and V is the applied voltage.

For safety, we limit the maximum voltage of encapsulated conductor lines 16 and 17 in the body to about 50 volts, such datum point limiting the maximum peak to peak displacement of a single piezoelectric element to about 0.1 microns. Thus, to achieve a total linear translation of 1 to 10 microns peak to peak will require a plurality of stacked piezoelectric elements, i.e. about 10-100. Those skilled in the art will recognize that to optimize the displacement of the stack of piezoelectric elements 3 for a given voltage, the piezoelectric elements 3 are arranged with alternating polarity such that all positive terminals are connected together in parallel, and all negative terminals are connected together in parallel. This arrangement is illustrated in more detail in FIG. 11.

Interface element 7 comprising an electrically non-conductive material is bonded to the bottom element of the piezoelectric element stack 3, attaching it to non-conductive insert 8. The interface element is sufficiently thick to prevent contact between the piezoelectric stack 3 and base ring 12 at any point in the vibrational excursions of the piezoelectric elements. The space inside hermetic housing 9 not occupied by inertial mass 2, piezoelectric elements 3, interface element 7, non-conductive insert 8, wires 16 and 17, and pins 13 and 14, contains at least some amount of an inert gas such as helium. This allows for hermetic leak detection of housing 9 using a helium leak detector.

Figure 1B:
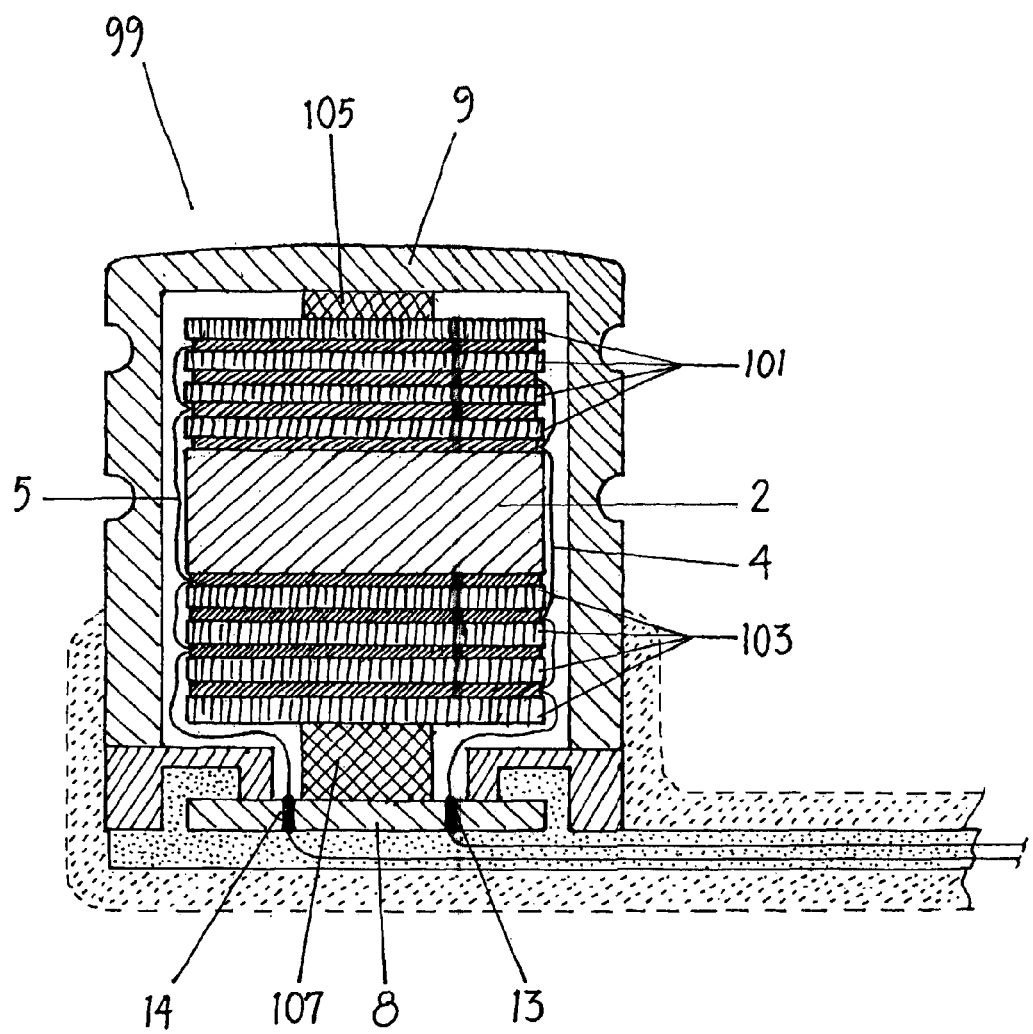
FIG. 1B shows a cross sectional view of an alternate embodiment of the inertial transducer encapsulated in a hermetic housing.

FIG. 1B shows a cross sectional view of an alternate embodiment 99 of the hermetically sealed inertial mass vibrator 1. In this embodiment the inertial mass 2 is attached on its top and bottom surface to a stack of piezoelectric elements 101 and 103. The upper stack 101 is attached via non-conductive interface element 105 to the top of the hermetic housing 9. The lower stack 103 is attached via interface element 107 to the nonconductive insert 8 in the base of the hermetic housing as in FIG. 1A. The piezoelectric elements in stacks 101 and 103 are electrically connected by wires 4 and 5 to electrical connector pins 13 and 14. The polarities of the piezoelectric elements in the stacks are arranged so that a voltage applied across the pins results in an expansion in one stack and a corresponding contraction in the other stack so that both stacks act to move the inertial mass 2 in the same direction, either up or down depending on the polarity of the applied voltage. The advantage of the alternate embodiment of FIG. 1B over the preferred embodiment of FIG. 1A is that the use of two piezoelectric stacks to push and pull simultaneously on the inertial mass provides twice the force on the inertial mass. This may result in an increased displacement of the inertial mass in cases where a single piezoelectric stack does not apply sufficient force to move the inertial mass to the limits set by the maximum displacement of the piezoelectric material given the applied voltage. The use of two stacks may also increase the reliability of the transducer against fracture of the piezoelectric material or of the connective bonding elements in the piezoelectric stack due to the disruptive force of the inertial mass pulling on the stack at the top of its vibrational cycle.

Figure 1C:
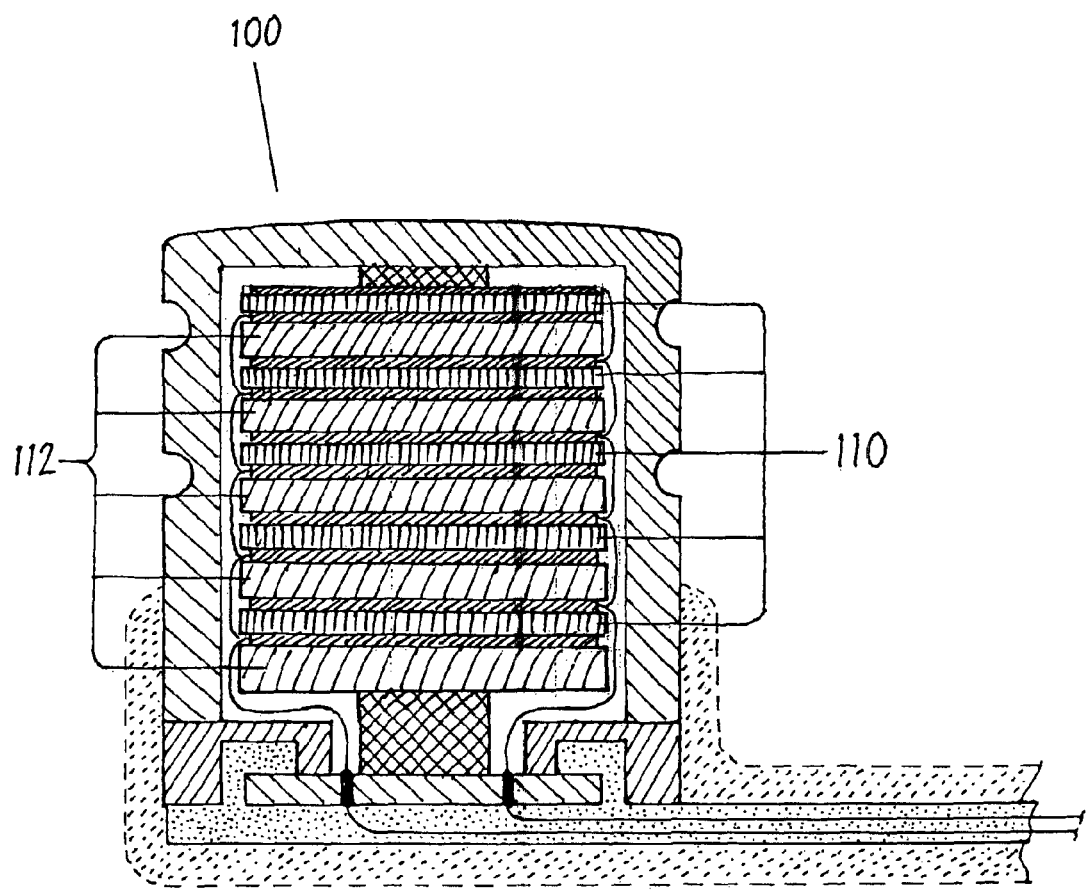
FIG. 1C shows a cross sectional view of another alternate embodiment of the inertial transducer encapsulated in a hermetic housing.
Figure 1D:
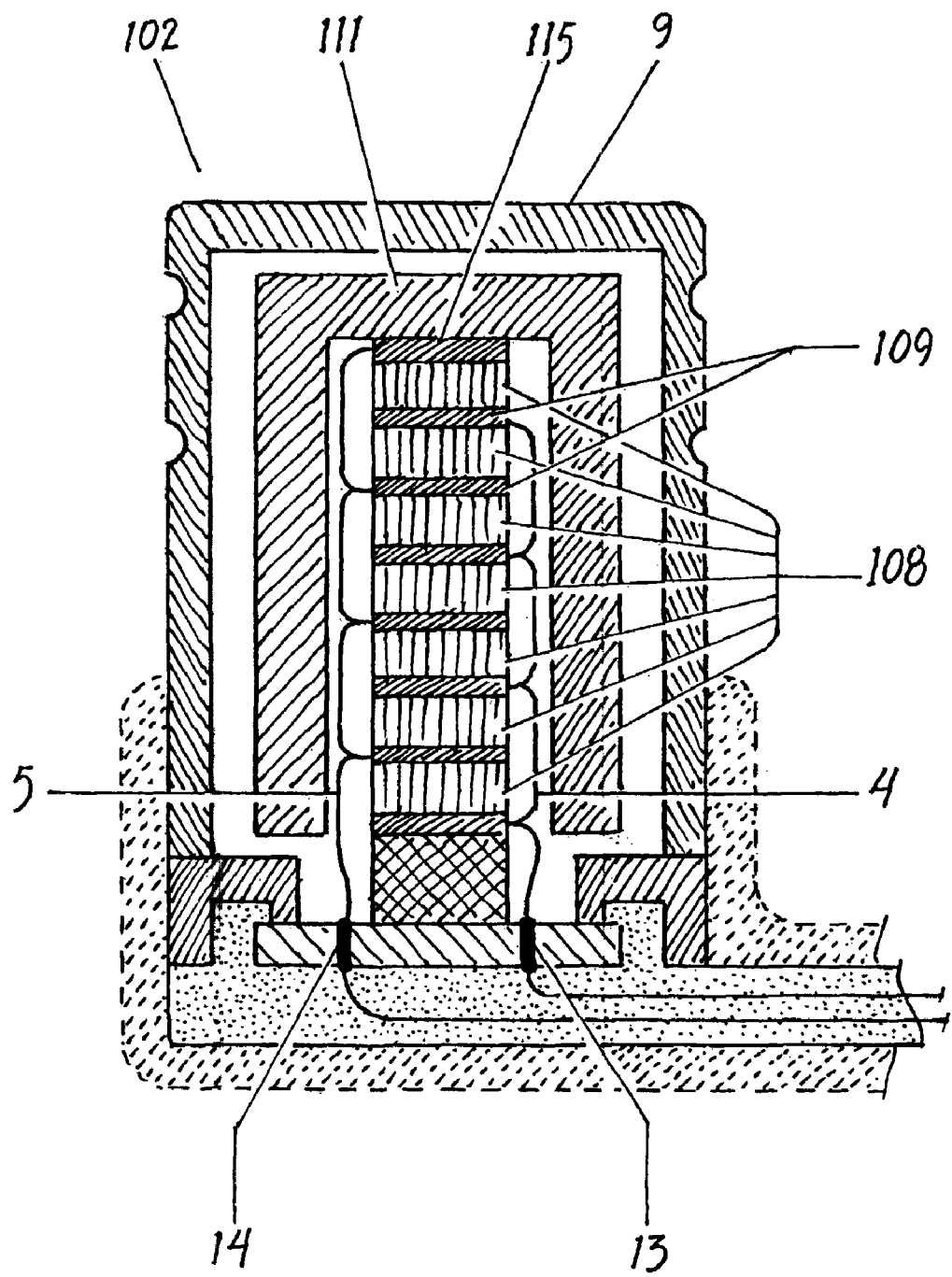
FIG. 1D shows a cross sectional view of another alternate embodiment of the inertial transducer encapsulated in a hermetic housing.
Figure 1E:
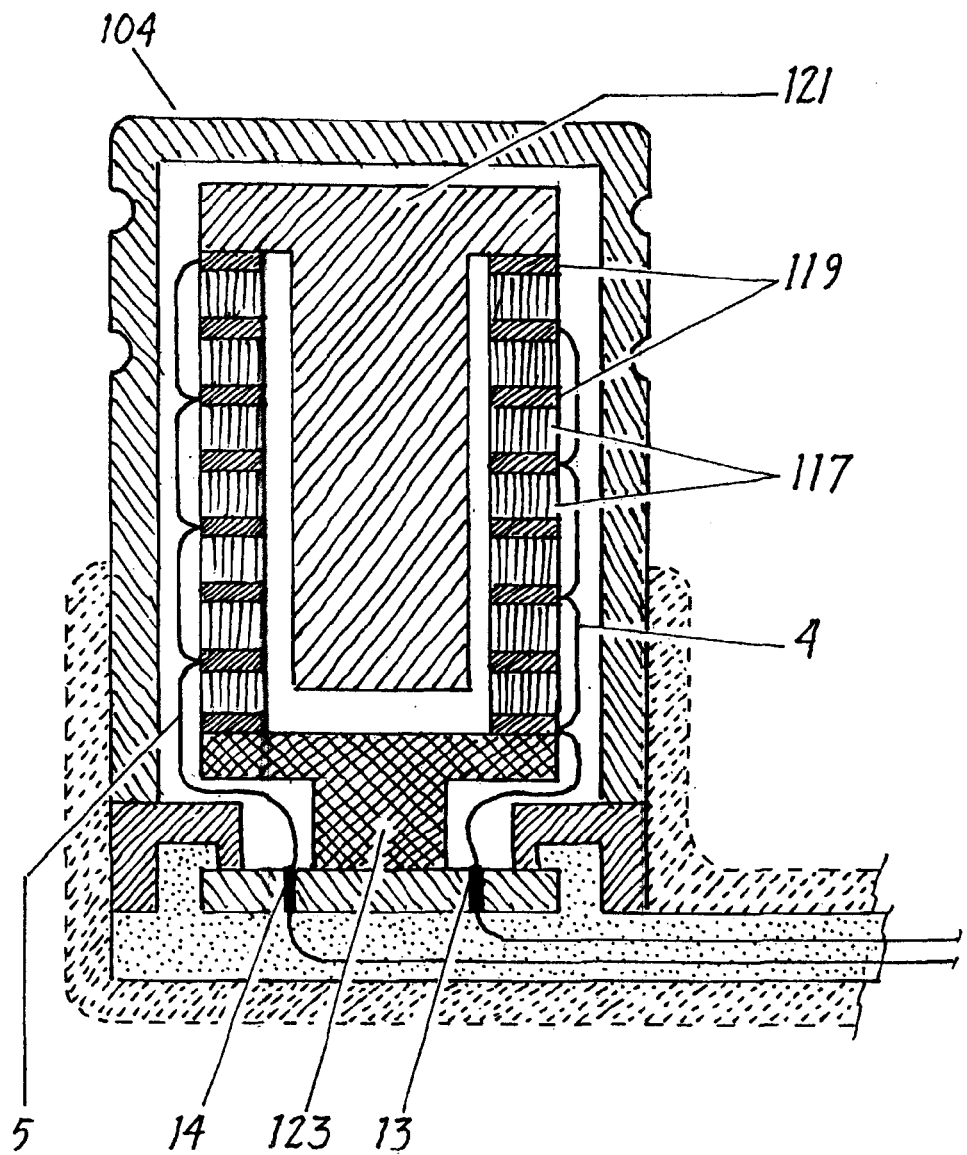
FIG. 1E shows a cross sectional view of another alternate embodiment of the inertial transducer encapsulated in a hermetic housing.
Figure 1F:
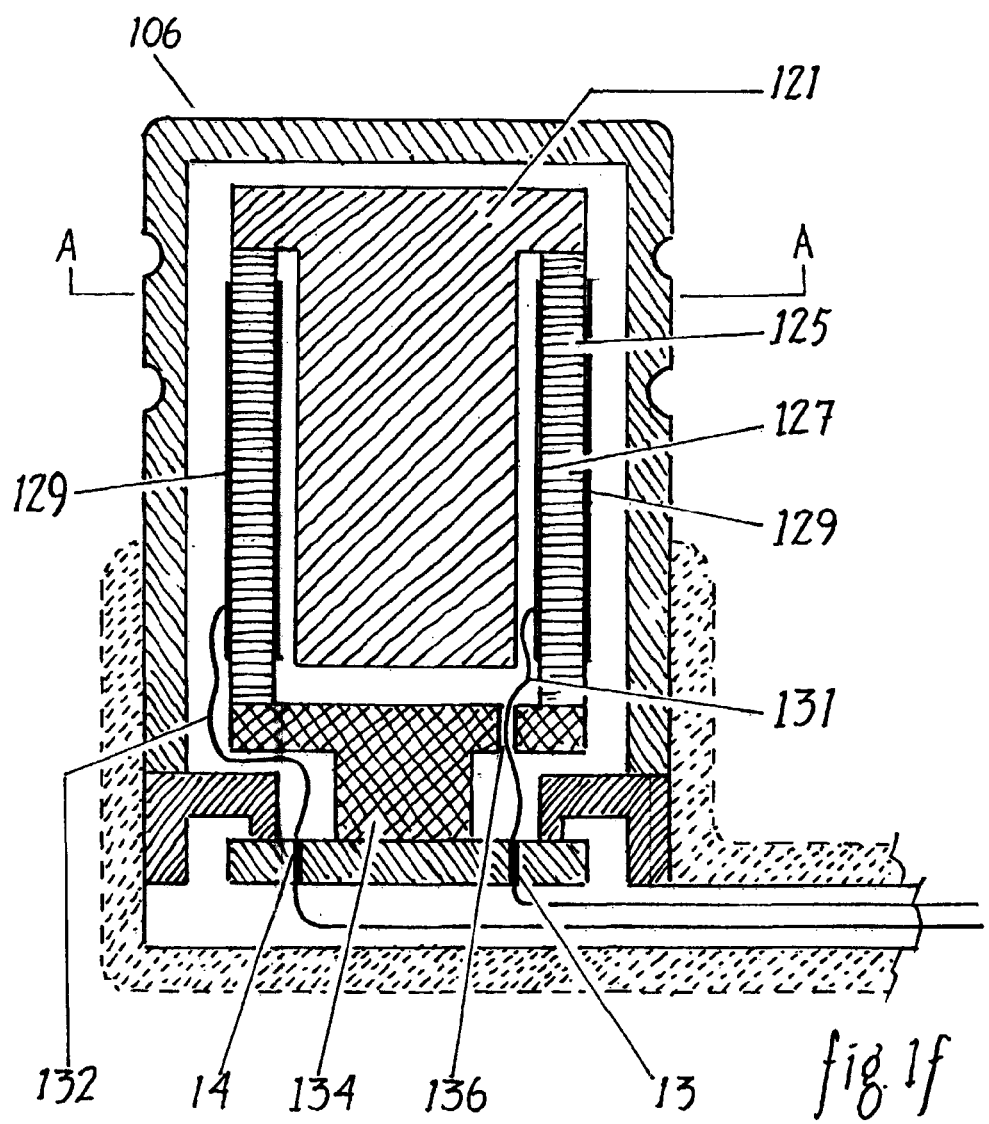
FIG. 1F shows a cross sectional view of another alternate embodiment of the inertial transducer encapsulated in a hermetic housing.
Figure 1G:
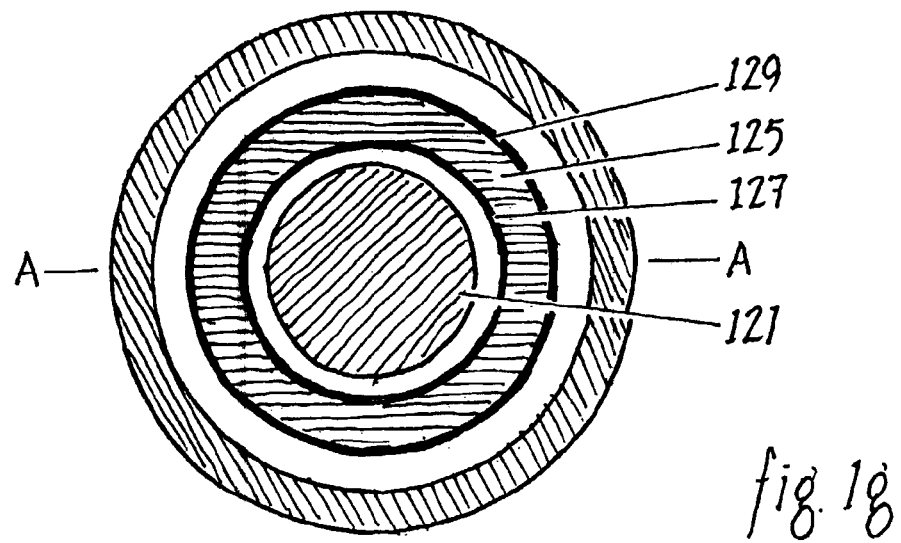
FIG. 1G shows a cross sectional view through line "A" of the inertial transducer shown in FIG. 1F.

FIG. 1C shows a further alternate embodiment 100 of the hermetically sealed inertial mass vibrator 1. In this embodiment the inertial mass is dispersed throughout piezoelectric stack 110 as a series of layers 112. The inertial mass is constituted of some electrically conductive and dense material such as gold or platinum so that the interleaved layers 112 constitute part of the conductive bond layer 6 referred to in FIG. 1A. The advantage of the alternate embodiment of FIG. 1C over the preferred embodiment of FIG. 1A is that the inertial mass is integrated with the piezoelectric stack, eliminating the need for a separate inertial mass element.

Figure 2:
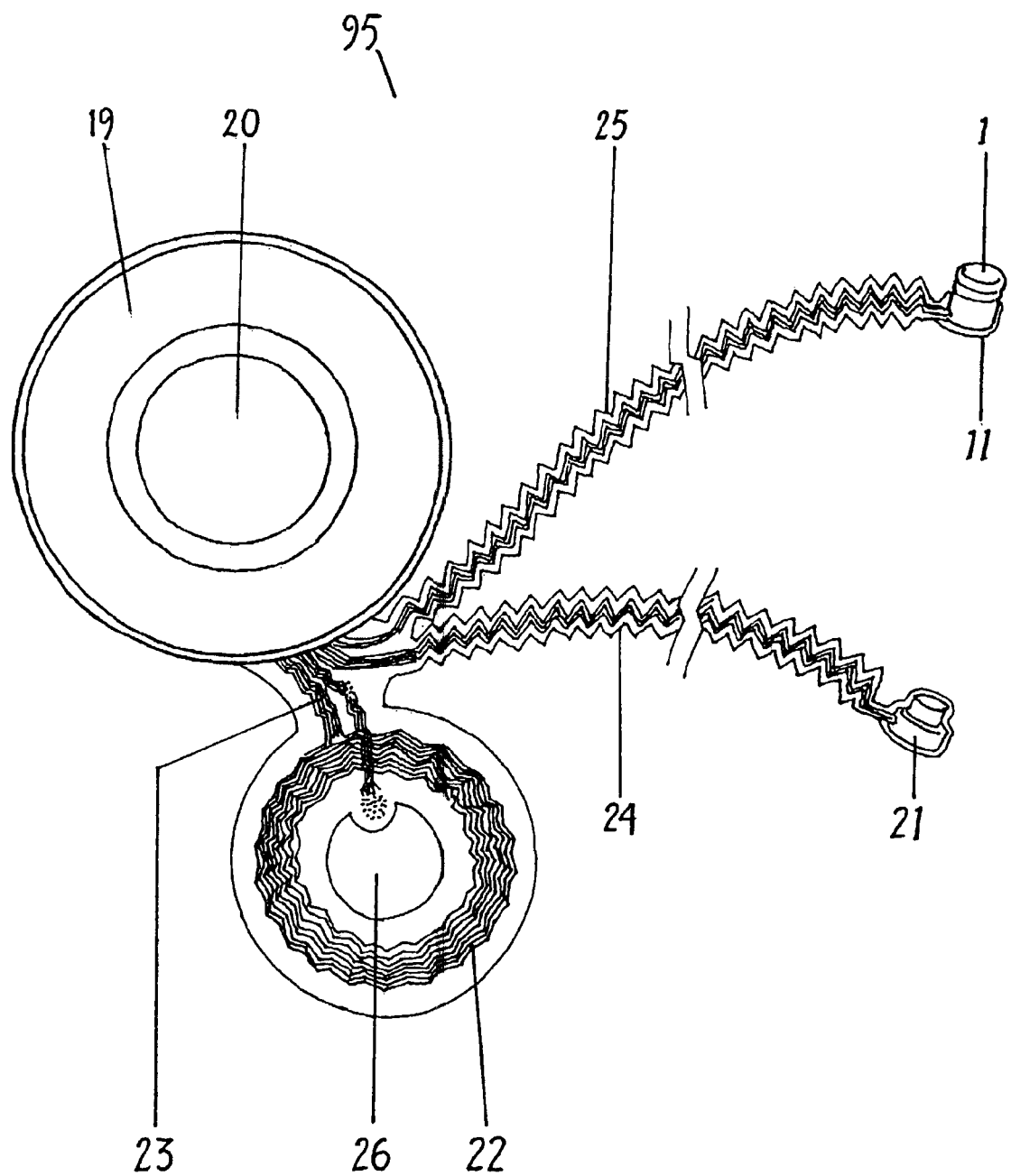
FIG. 2 illustrates a totally implantable hearing prosthesis comprised of a main housing containing control electronics and battery, which housing is operatively connected to an RF coil, an encapsulated microphone, and a transducer, via connector lines.

In the preferred embodiment, the inertial mass vibrator 1 illustrated in FIG. 1A forms an integral component of a totally implantable hearing prosthesis 95, as illustrated in FIG. 2. The totally implantable hearing prosthesis 95 is comprised of a main housing 19, containing control electronics, on-off switch 20 and battery, which housing 19 is operatively connected to a transducer 1, a hermetically sealed microphone 21, and an RF coil 22 via connector cables 23, 24 and 25 respectively. The housing 19 contains a manually activatable on-off switch 20 located at the proximal surface of the housing, such switch actuation similar to that described in U.S. Pat. No. 6,358,281 B1 and U.S. patent application Ser. No. 10/012,341, included herein by reference. The base of the vibrator 1 is preferably coated with a compliant material 11, such as silicone, to create an impedance mismatch barrier to the transfer of vibrational energy from the base into bone surrounding the compliant material. Such impedance assists to direct the transducer vibrations preferentially to the portion of the vibrator 1 that is osseointegrated in the bone surrounding the otic capsule. Similarly, the hermetically sealed microphone 21 is preferably encapsulated in a compliant material, such as silicone, such encapsulation creating an acoustic impedance between the microphone 21 and the surrounding bone. Since any vibrations induced by the vibrator 1 can create a feedback effect through bone, that would be sensed by the microphone 21, acoustic isolation against such feedback signal will improve the implantee's hearing percepts. Internal RF coil 22 is used for transcutaneous communication between a similar external coil (not shown) for battery charging and monitoring functions with the electronics in the main housing 19. A magnet 26 can be located within the coil to help align the internal RF coil 22 with the external coil.

Figure 3:
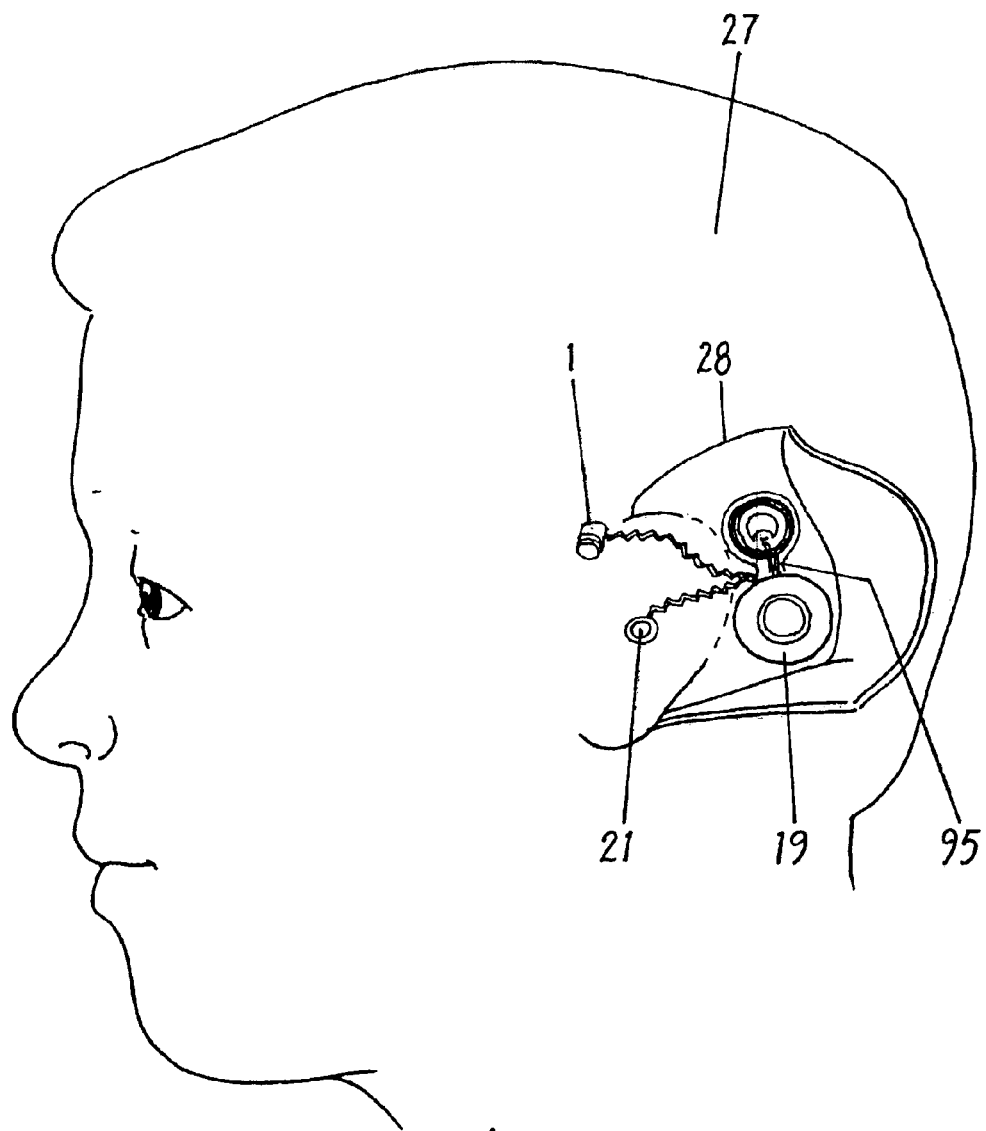
FIG. 3 is a lateral view of the left side of the head showing the hearing prosthesis in place, the view also illustrating one embodiment of an incision on the head to gain access for implantation.

The totally implantable hearing prosthesis 95 shown in FIG. 2 can be implanted as shown in FIG. 3, which is a lateral view of the left side of the head 27 showing the hearing prosthesis 95 in place, the view also illustrating one embodiment of an incision 28 on the head 27 to gain access for implantation. The surgical orientation of the prosthesis 95 is for illustration purposes only. A possible surgical method, adapted to implant a vibrator substantially between and/or among the semicircular canals and/or vestibule without breaching the canals or vestibule, comprises the steps of: forming an approximate two inch incision in the postauricular skin crease and exposing the surface of the mastoid bone; drilling through the mastoid until the antrum is found; thinning the posterior canal wall, identifying the horizontal canal and drilling out a cavity superior to it; and then recessing the cavity and packing the housing of the device into the cavity using bone paste so as to promote osseointegration. Those skilled in the art will recognize that the other locations and orientations of the main housing 19, vibrator 1 and hermetically sealed microphone 21 are possible, without deviating from the functionality of the prosthesis 95. The embodiment illustrated in FIG. 3 shows the hermetically sealed microphone 21 positioned in the area of the bony wall of the auditory canal, similar to U.S. patent application Ser. No. 09/499,376, included herein by reference.

Figure 4:
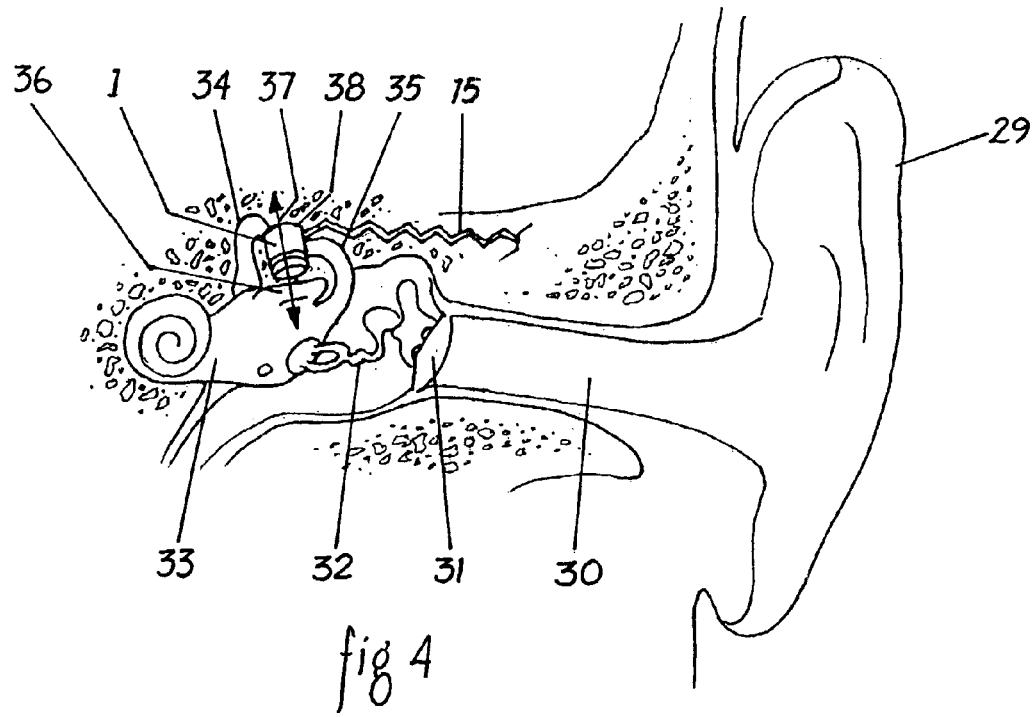
FIG. 4 is a coronal view of the left ear illustrating important anatomical features of the ear, including the ear canal, cochlea and the semicircular canals with the implanted transducer housing oriented such that its axis of motion is perpendicular to the plane of the horizontal canal.
Figure 5:
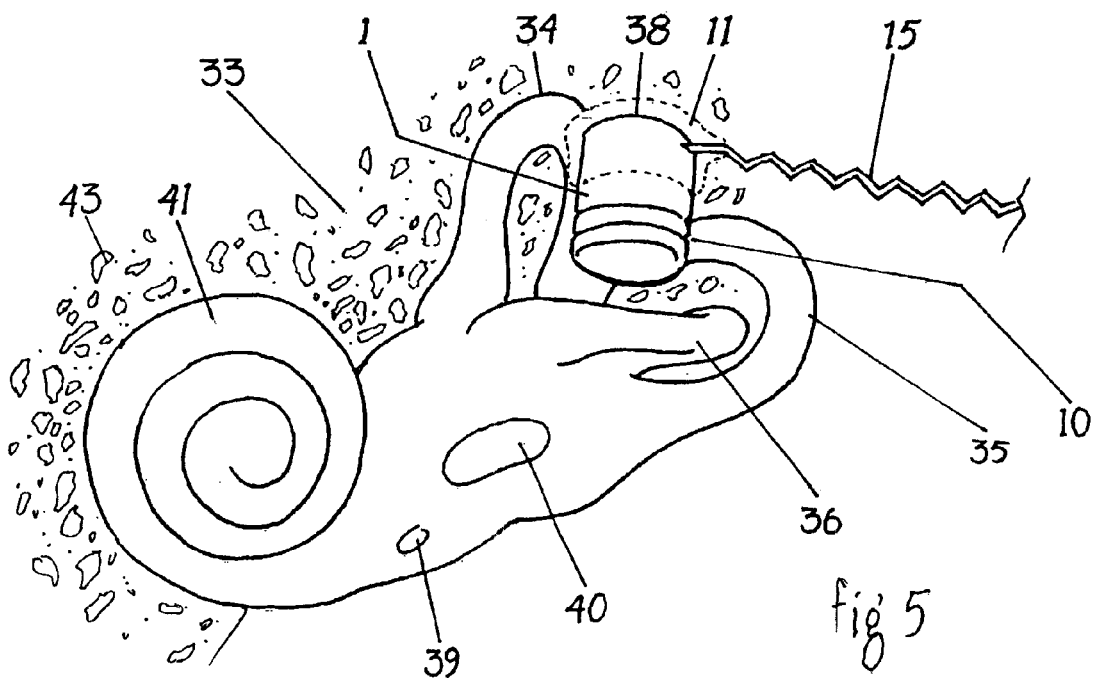
FIG. 5 is an enlarged view of the left otic capsule and shows the transducer, osseointegrated and oriented such that its axis of motion is perpendicular to the plane of the horizontal canal, with the vibrational mass sitting closer to the horizontal canal than the piezoelectric crystals.

One aspect of the current invention is the location of the vibrator 1 close to the semicircular canals. One embodiment of the positioning of the vibrator 1 is illustrated in FIG. 4, which is a coronal view of a left ear including the pinna 29, external auditory canal 30, eardrum 31, middle ear 32 and inner ear 33. The vibrator 1 is positioned within the intercanalicular space defined by the superior 34, posterior 35 and lateral 36 semicircular canals. The vibrator is preferentially oriented such that its vibrational axis of motion 37 is perpendicular to the plane of the horizontal semicircular canal, with its base 38 positioned away from the horizontal canal. Bioinert cable 15, for the purposes of conducting electrical current, exits from the base 38 of the vibrator 1. A more detailed view of the positioning of the vibrator 1 is illustrated in FIG. 5, which is an enlarged view of a left inner ear 33, showing the vibrator 1 in place within the intercanalicular space of the otic capsule. The superior 34, posterior 35 and lateral 36 semicircular canals are shown, as is the round window 39, oval window 40 and cochlea 41. The housing of the vibrator 1 shows rings 10 that are radially disposed along a portion of the outside cylindrical wall of the housing, so as to assist at least part of the housing wall to osseointegrate within the bone surrounding the semicircular canals. The base of the vibrator 38 and part of the cylindrical wall is coated with a substantially compliant material 11, to prevent the transfer of vibrational energy from the base of the vibrator 38 to the surrounding bone 43. Bioinert cable 15, for the purposes of conducting electrical current, exits from the vibrator base 38.

Figure 6:
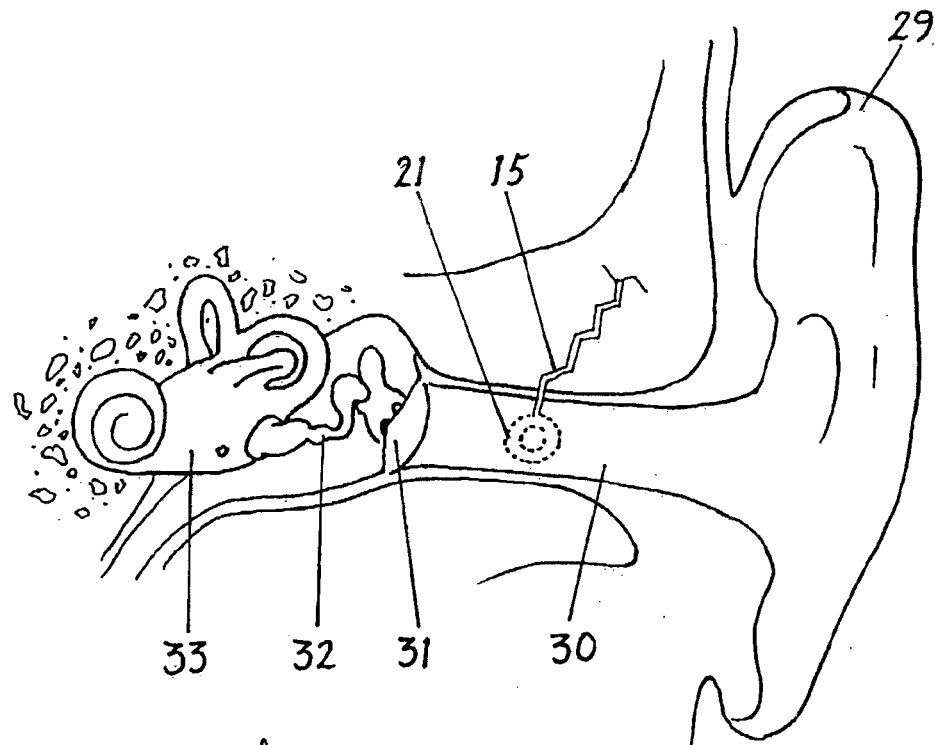
FIG. 6 shows a coronal view of the left ear with a microphone implanted in bone and under the skin of the posterior wall of the ear canal.

In one of the embodiments of the totally implantable hearing prosthesis 95 shown in FIG. 3, a hermetically sealed microphone 21 is implanted in the external auditory canal. FIG. 6 illustrates such an embodiment, and is a coronal view of a left ear, including the pinna 29, external auditory canal 30, eardrum 31, middle ear 32, and inner ear 33 and shows the implanted microphone 21, hermetically sealed within a biocompatible housing, in place under skin in the posterior wall of the external auditory canal 30. At least part of the housing contains one or more circular and/or spiral grooves around its outside wall, to aid with osseointegration of the wall to surrounding bone and tissue. At least part of the housing encapsulating the microphone is coated with a compliant material to increase the impedance to acoustic waves between the microphone housing and the surrounding bone and tissue. Bioinert cable 15, for the purposes of conducting electrical current, exits from the base of the microphone housing.

Figure 7:
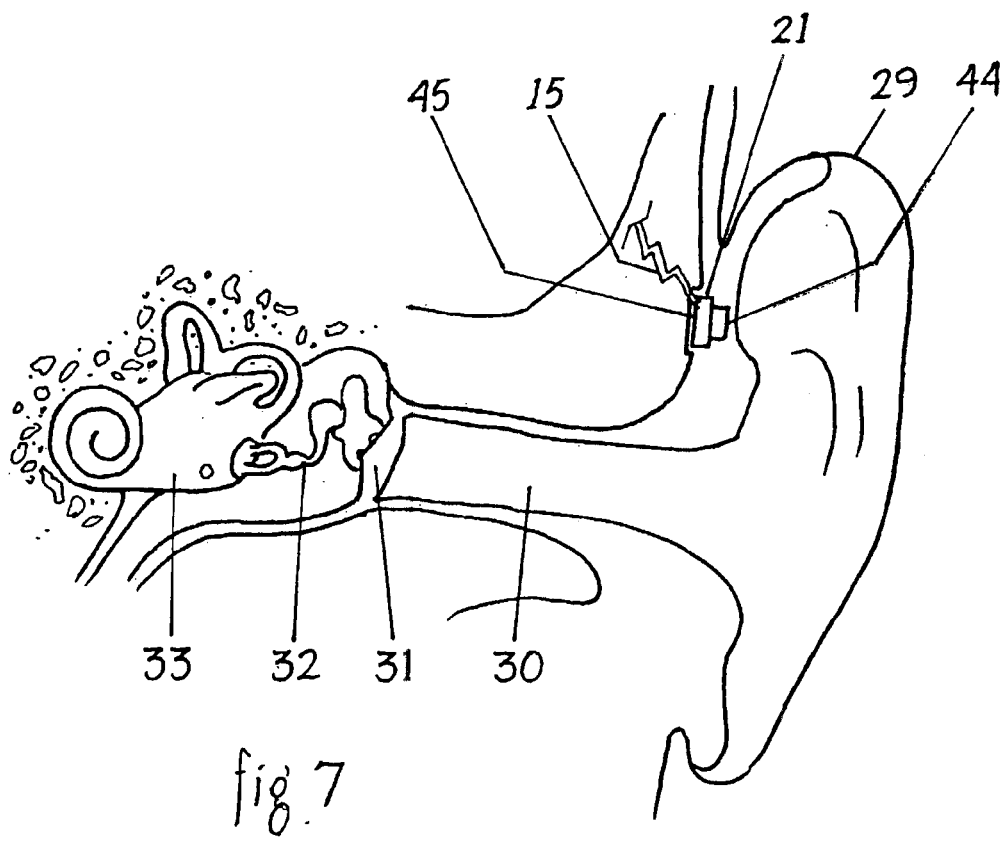
FIG. 7 shows a coronal view of the left ear with a microphone implanted in bone and under the skin in the cymba concha of the pinna.

In an alternate embodiment of the totally implantable hearing prosthesis 95 referred to in FIG. 3, an implantable microphone 21 is implanted in the cymba concha 44 of the pinna 29. FIG. 7 illustrates this embodiment, and is a coronal view of a left ear, including the pinna 29, external auditory canal 30, eardrum 31, middle 32, and inner ears 33 and shows the implanted microphone 21, hermetically sealed within a biocompatible housing, in place, under skin in the cymba concha 44 of the pinna 29. At least part of the housing contains one or more circular and/or spiral grooves around its outside wall, to aid with osseointegration of the wall to surrounding bone and tissue. At least part of the housing encapsulating the microphone is coated with a compliant material to increase the impedance to acoustic waves between the microphone housing and the surrounding bone and tissue. Bioinert cable 15, for the purposes of conducting electrical current, exits from the microphone housing base 45 and attaches to the sound processing package implanted under skin at the side of the head. A possible surgical method, adapted to implant an implantable microphone 21 substantially within or near the cymba concha 44 of the pinna 29, comprises the steps of: approaching the cymba 44 through a postauricular skin incision; raising the perichondrium on the medial side of the cymba 44; removing a circular core of cartilage from the auricular cartilage while not disturbing the lateral perichondrium; inserting the implantable microphone and suturing the medial layer of perichondrium and the skin to cover the microphone and keep it in place.

Figure 8:
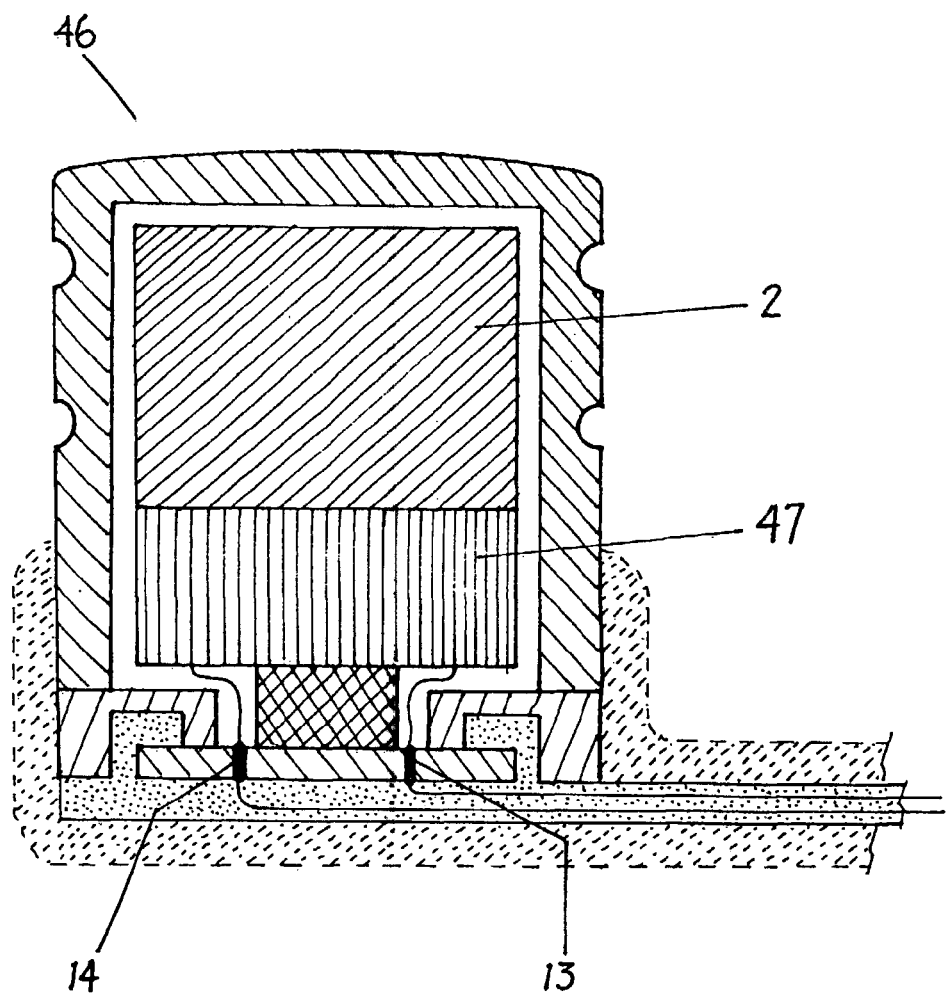
FIG. 8 shows a cross sectional view of an alternate embodiment of an inertial transducer encapsulated in a hermetic housing.

There are alternate mechanisms for vibrating the inertial mass 2 of the hermetically sealed inertial mass vibrator 1 shown in FIG. 1A. FIG. 8 shows an alternate vibrator 46 in which the stack of piezoelectric elements 3 shown in FIG. 1 is replaced by a generalized vibrating element 47 which causes movement of inertial mass 2 in response to an applied electrical signal on pins 13 and 14. The generalized vibrating element 47 may substantially consist of, but is not limited to, the following:

a piezoelectric bimorph utilizing the bending of a plate due to the electrically induced differential expansion and/or contraction of two or more elements comprising the plate to produce a translation.

a magnetostrictive material such as nickel together with means to generate a magnetic field from applied electrical signal, causing the material to expand and contract in response to the field.

an electromagnetic transducer comprising a material with permanent magnetic field together with means of generating a magnetic field from applied electric signal, arranged such that a force produced by these fields results in a translation.

an electrostatic transducer in which applied electrical signal is applied to two or more capacitive surfaces such that the electrostatic force between the surfaces results in a translation.

a thermal transducer comprising means of generating localized heat from applied electrical signal together with element for producing translation in response to the localized heat. The element may comprise but is not limited to:

a bimorph that flexes in response to heat due to differential thermal expansion between two or more constituent elements;

a substantially homogeneous material with high coefficient of thermal expansion;

a material that undergoes reversible phase transition in response to localized heat resulting in volume change, such as a contained liquid that vaporizes to form a gas bubble around the localized heat source.

Figure 9:
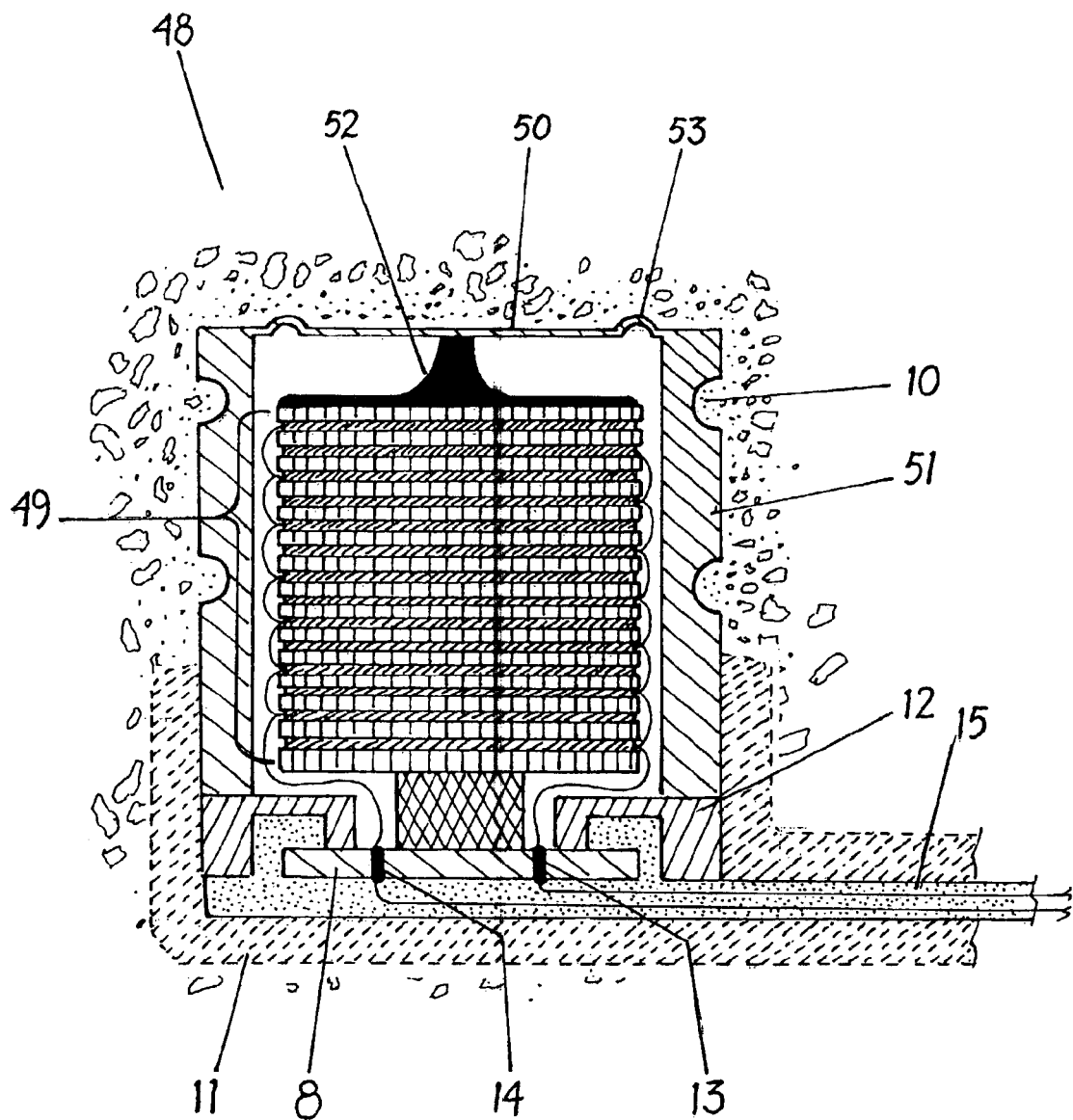
FIG. 9 illustrates a cross sectional view of an embodiment of a transducer encapsulated in a hermetic housing, where both ends of the transducer are firmly attached.

Yet another alternate vibrator 48 having a stack of piezoelectric elements 49 secured at both ends is shown in FIG. 9. In this alternate transducer, the inertial mass 2 shown in FIG. 1 is replaced by increasing the height of the piezoelectric stack 49 and connecting it to a flexible top 50 of hermetic container 51 by means of a connecting element 52.

A core aspect of this alternate embodiment is that the flexible top 50 moves up and down relative to the rest of the hermetic container due to expansion and contraction of the piezoelectric stack 49 in response to electrical signals applied to pins 13 and 14. The hermetic container is designed to be securely held by the bony structure surrounding the semicircular canals by means of osseointegration rings 10, and is placed so that the flexible top contacts a layer of bone surrounding the semicircular canals. Vibrations of the flexible top 50 at acoustic frequencies substantially between 100 Hz and 8000 Hz are transmitted through the layer of bone causing the perilymph in the semicircular canals and cochlea to vibrate, thereby inducing hearing percepts in the implantee.

Flexible top 50 is preferably composed of titanium foil of sufficient thickness to maintain hermeticity of the container while thin enough to be flexible. Such thickness is typically about 10 to 100 microns. To further increase flexibility, one or more ridges 53 may be impressed in the flexible top 50, the ridges 53 taking the form of one or more concentric rings 53, which are impressed into the flexible top 50. The flexible top 50 is attached to the walls of hermetic container 51 by attachment means such as laser welding suitable to produce a hermetic seal.

Electrically non-conducting connecting element 52 is bonded to substantially the center of the top surface of piezoelectric stack 49. The connecting element 52 may be bonded to the flexible top 50 or alternately be maintained in contact with the flexible top 50 by means of transducer design whereby a positive pressure exists between the connecting element 52 and the flexible top 50 for all excursions of the piezoelectric stack 49 in response to electrical signals on pins 13 and 14.

As described in FIG. 1A, a base ring 12, non-conductive insert 8, and bioinert cable 15 are attached at the base of the hermetic housing 51. The base of the hermetic housing 51, together with base ring 12, and cable 15, are coated with a compliant material 11, preferably silicone, or a silicone derivative material, which material acts as an impedance mismatched barrier to the transfer of vibrational energy from the base end into bone surrounding such compliant material.

Figure 10:
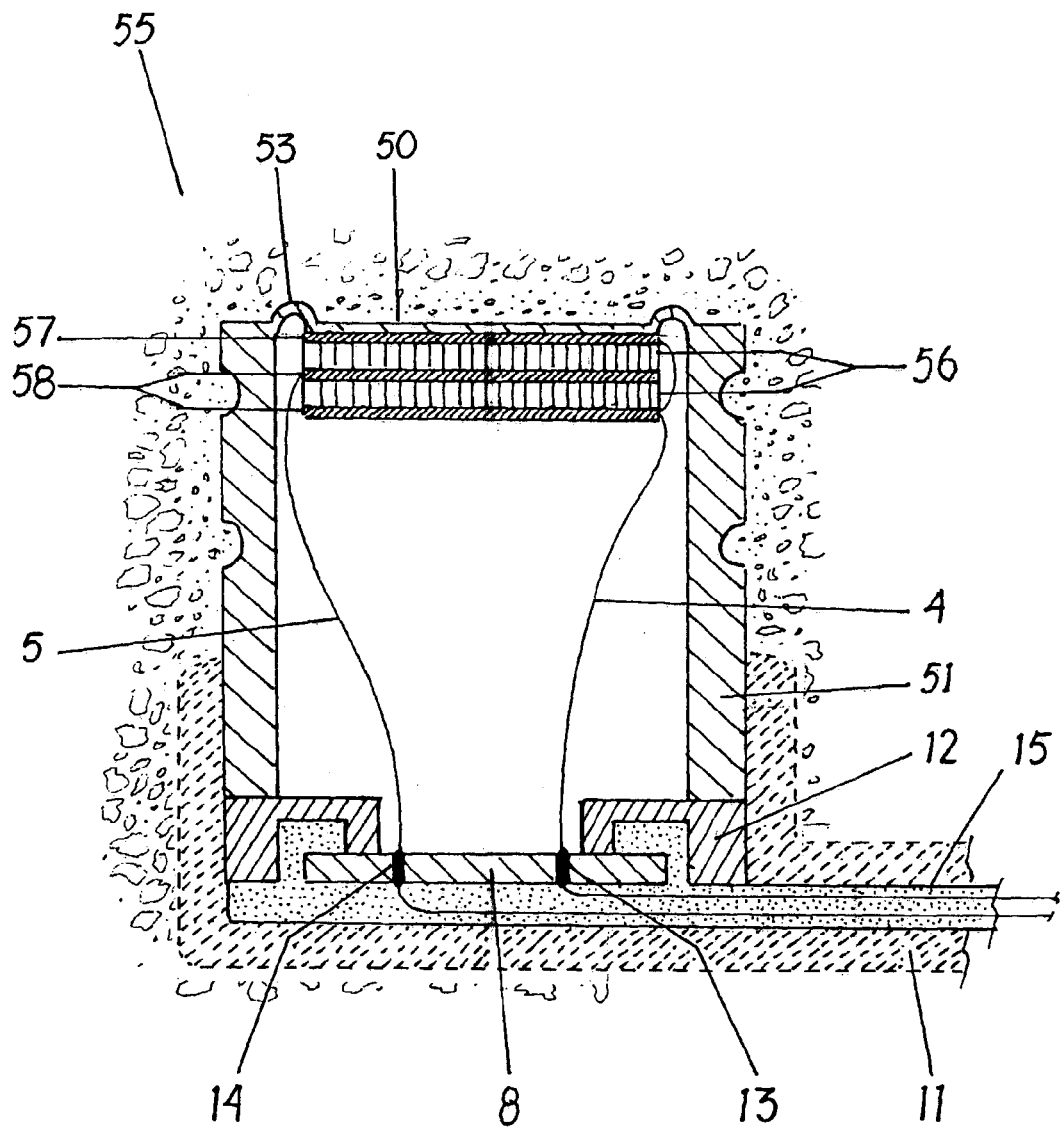
FIG. 10 illustrates a cross sectional view of a transducer encapsulated in a hermetic housing, where the transducer comprises a piezoelectric bimorph strip.

Yet another alternate transducer 55 having a piezoelectric bimorph element 56 attached to a flexible top 50 of a hermetic container 51 is shown in FIG. 10. In this alternate embodiment a piezoelectric element 56 is bonded to electrically non-conductive layer 57 which is in turn bonded to flexible top 50. The top and bottom surfaces of the piezoelectric element are coated with electrically conductive layers 58 which are connected by means of wires 4 and 5 to pins 13 and 14. A voltage applied between the pins causes the piezoelectric element to expand or contract in the longitudinal direction according to the formula:

$$?L = d_{31} V/T$$

where ?L is the change in the length of the piezoelectric element, T is its thickness, V the applied voltage, and $d_{31}$ the piezoelectric coefficient for deformation perpendicular to the applied electric field.

Piezoelectric element 56 is constrained by its attachment to nonconductive layer 57 and flexible top 50 both of which tend to maintain their normal longitudinal dimensions. The result of an expansion or contraction in the length of the piezoelectric element 56 is a bending of the piezoelectric element 56, together with the nonconductive layer 57 and the flexible top 50. An expansion of the piezoelectric element 56 produces concave bending with the center of the flexible top 50 moving down relative to hermetic container 51, while a contraction produces convex bending with the center moving up.

The flexible top 50 is preferably composed of titanium foil with ridges to increase flexibility as described in FIG. 9.

The operational principle of this alternate transducer 55 is similar to that of alternate transducer 48 described in FIG. 9 in that the walls of hermetic container 51 are securely held by the bony structure surrounding the semicircular canals while vibrations of flexible top 50 in response to electrical signals on pins 13 and 14 transmits vibrations through a thin bony layer into the perilymph in the semicircular canals and cochlea.

As described in FIG. 1A, a base ring 12, non-conductive insert 8, and bioinert cable 15 are attached at the base of the hermetic housing 8. The base of the hermetic housing 8, together with base ring 12, and cable 15, are coated with a compliant material 11, preferably silicone, or a silicone derivative material, which material acts as an impedance mismatched barrier to the transfer of vibrational energy from the end into bone surrounding such compliant material.

Figure 11A:
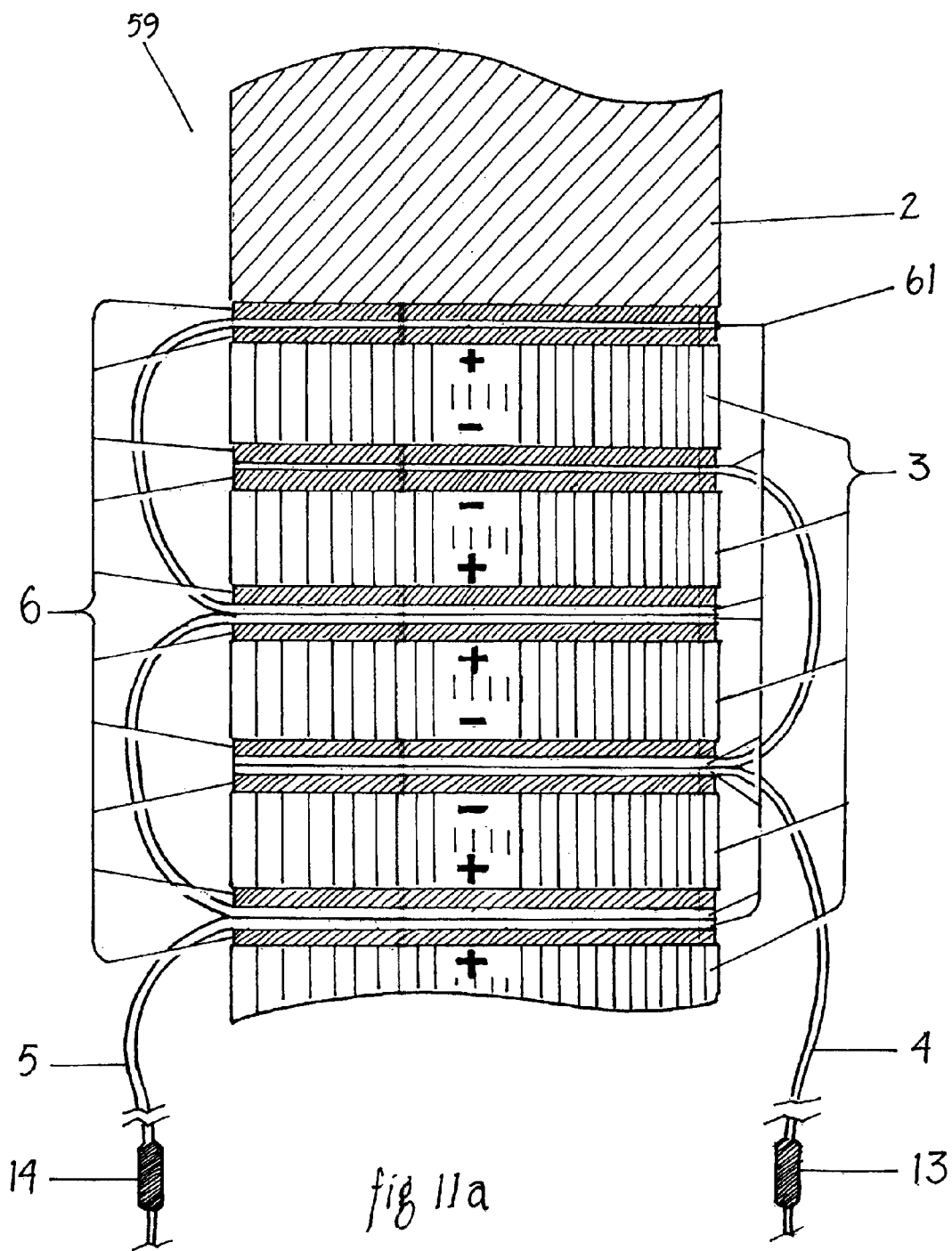
FIG. 11A is a large scale sketch showing a plurality of transducer elements, one connected to the other, with the polarity of such transducer elements oriented to have like polarities electrically connected in parallel.

A detailed view of the piezoelectric elements 3 of FIG. 1A and the piezoelectric stack 49 of FIG. 9 is shown in FIG. 11A. The stack 59 is comprised of a plurality of elements as follows: piezoelectric elements 3 coated on top and bottom surfaces with an electrically conductive layer 6, electrically conductive bonding layers 61 connected by wires 4 and 5 to pins 13 and 14.

Piezoelectric elements 3 are comprised of disks of material with a high piezoelectric coefficient $d_{33}$ such as PZT, PKM, barium titanate, or lead titanate zirconate. The piezoelectric elements 3 are stacked with alternating polarities as indicated by the + and − symbols adjacent to the top and bottom surface of each element. This alternating polarity results in the positive surface of each element facing the positive surface of the adjacent element and likewise for the negative surfaces, facilitating the electrical connection of all positive surfaces to pin 14 and all negative surfaces to pin 13 as shown. Those skilled in the art will recognize that the amplitude of expansion and contraction of each piezoelectric element 3 is proportional to the applied voltage and to $d_{33}$ in the limit of low applied voltage, but is independent of the thickness of the element. Therefore the piezoelectric elements 3 are preferably constructed as thin as possible without degrading the mechanical or piezoelectric properties of the material, in this way maximizing the number of elements in the stack and hence the maximum displacement for a given applied voltage. Typical element thickness is about 10 to 100 microns.

Electrically conductive layers 6 coated on top and bottom surfaces of piezoelectric elements 3 ensure that the applied voltage is effective over the entire surface of the elements. The conductive layer is applied during fabrication of the piezoelectric material and is typically composed of silver or aluminum with a thickness of about 0.1 to 10 microns.

Figure 11B:
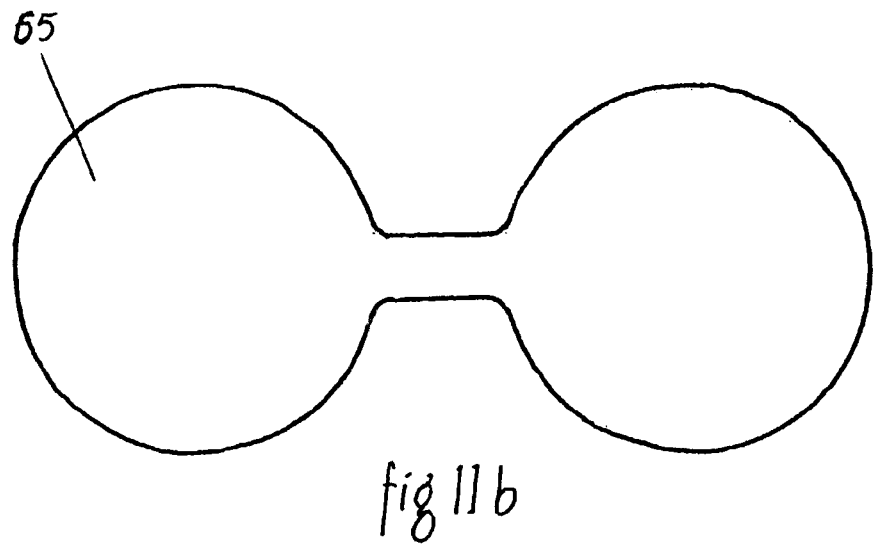
FIG. 11B is a sketch of an etched metal clip.
Figure 11C:
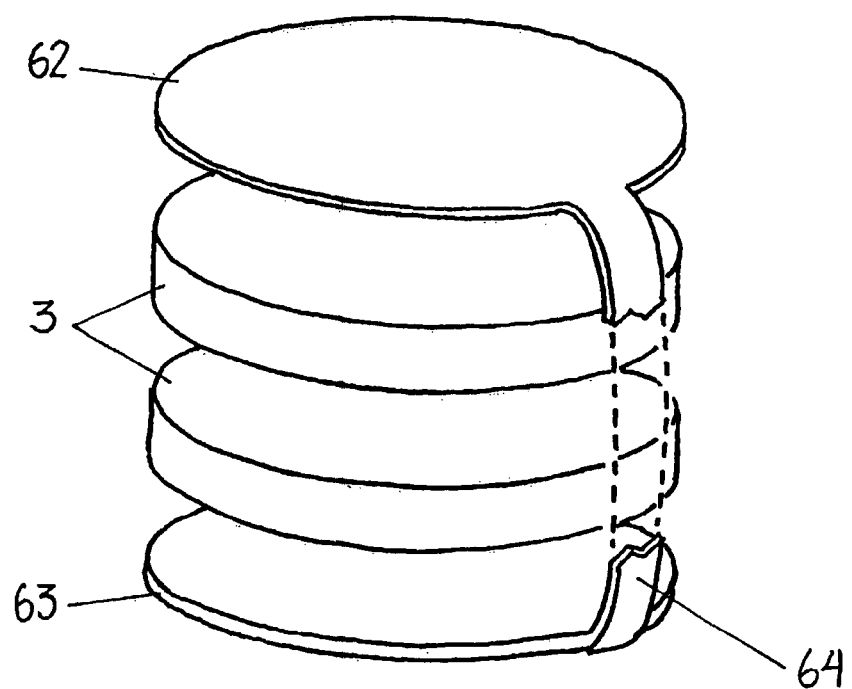
FIG. 11C is a sketch of an etched metal clip bent to form bonding layers in a piezoelectric stack.
Figure 11B:
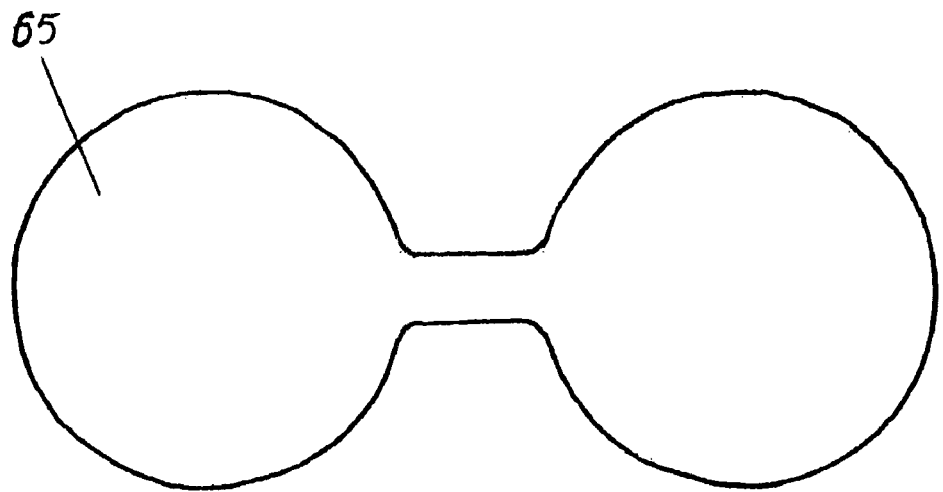
Figure 11C:
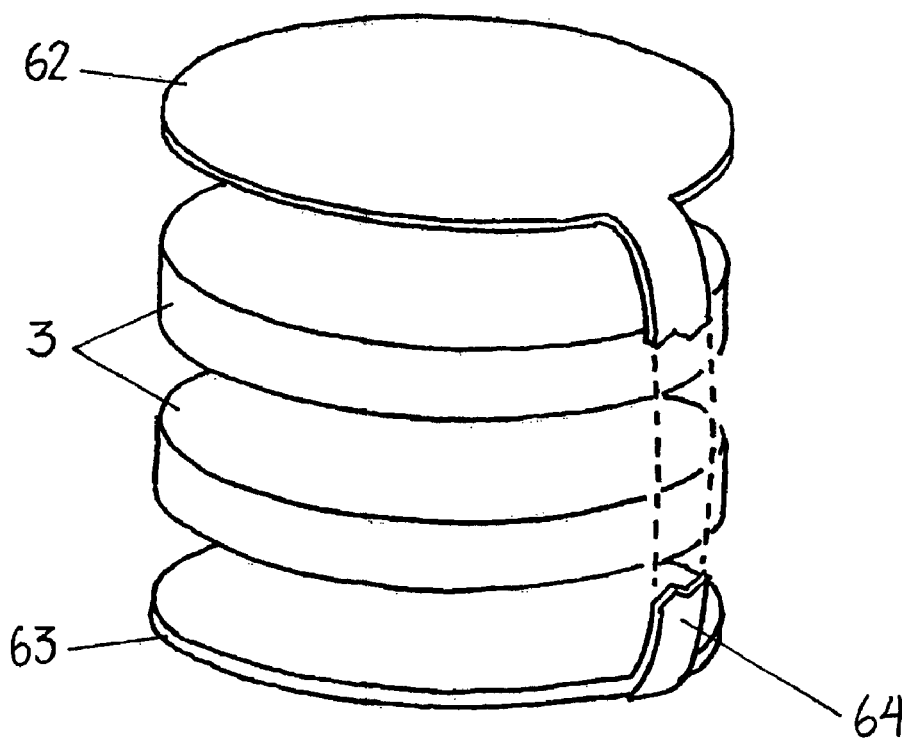

Electrically conductive bonding layers 61 are inserted between adjacent piezoelectric elements 3 and serve to connect the elements electrically and mechanically. The bonding layer 61 is comprised of a material capable of mechanical adhesion to the coated surfaces of the elements with the application of bonding stimulus such as heat or pressure. Those skilled in the art will recognize that a plurality of solders exist which melt and bond to various surfaces at various temperatures. Alternatively a soft metal such as gold may be used as the bonding layer, with a thin gold foil inserted between adjacent elements and bonded by pressing the elements together. A further function of the bonding layer 61 is to provide for electrical connections between piezoelectric elements 3 by wires 4 and 5. This may be achieved by arranging that a portion of the bonding layer 61 extends beyond the outer circumference of the element 3, providing a contact pad for attachment of the wires 4 and 5. In this case the contact pads for adjacent layers will optimally be arranged so as to extend on substantially opposite sides of the piezoelectric stack 59 to avoid short circuits and facilitate connection to opposite pins 13 and 14 as shown. An alternative design is illustrated in FIGS. 11B and 11C in which a pair of bonding layers 62 and 63 are joined by an electrically conductive link 64 to form an etched metal clip 65. This clip 65 is bent so as to form the bonding layers and wire connecting alternate layers of the piezoelectric stack as shown in FIG. 11C. In this embodiment the clip 65 is comprised of a metal foil about 1 to 100 microns thick. The metal may also be coated with bonding material such as solder, or not, as in the case of gold bonded by pressure.

Figure 12:
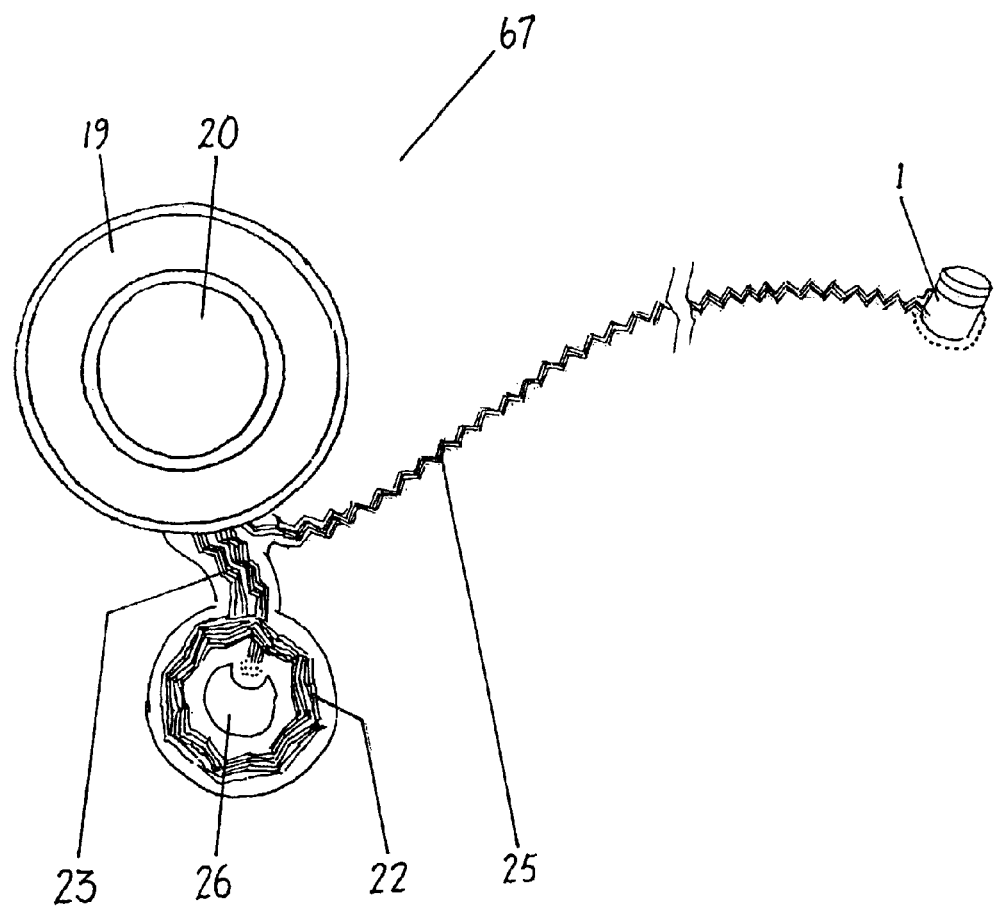
FIG. 12 illustrates a totally implanted tinnitus masker comprised of a main housing containing control electronics and a battery, which housing is connected to an RF coil and a transducer, via connector lines.

FIG. 12 illustrates a totally implanted tinnitus masker 67 comprised of a main housing 19 containing control electronics, an on-off switch 20 and battery, which housing 19 is connected to RF coil 22 and transducer 1 via connector cables 23 and 25, respectively. The base of the transducer 1 is preferably coated with a compliant material such as silicone, to create impedance mismatched barrier to the transfer of vibrational energy from the base into bone surrounding the compliant material. Such arrangement assists to direct the transducer vibrations preferentially to that portion of the transducer 71 that is osseointegrated in the bone surrounding the otic capsule. RF coil 22 is used for transcutaneous communication between a similar external coil (not shown) for battery charging and monitoring functions with the electronics in the main housing 20. A magnet 26 is located within internal RF coil 22 to help align it with an external coil (not shown) used to communicate with the internal coil 22.

Figure 13:
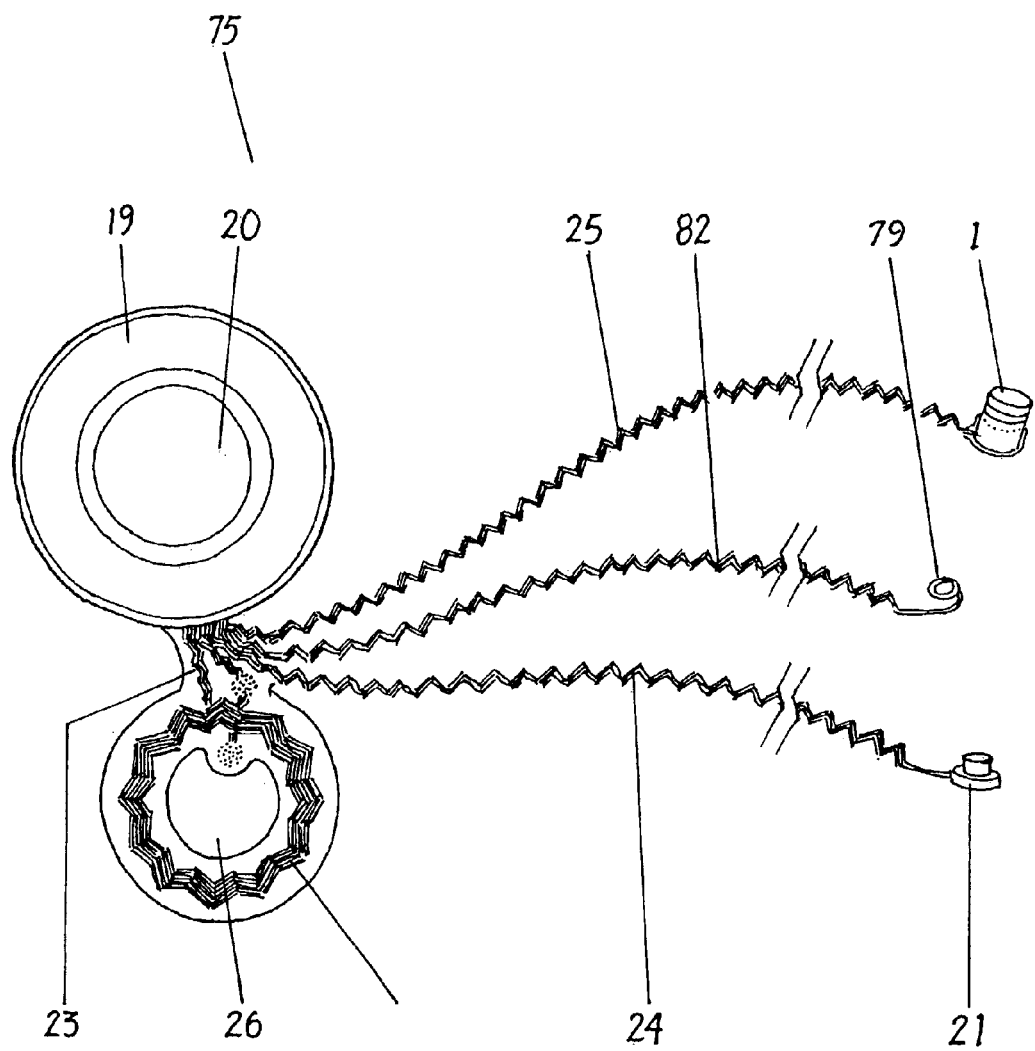
FIG. 13 illustrates a totally implantable hearing prosthesis comprised of a main housing containing control electronics and battery, which housing is operatively connected to an electrode array, RF coil, an encapsulated microphone, and a transducer, via connector lines.

FIG. 13 illustrates a totally implantable hearing prosthesis 75 comprised of a main housing 19 containing control electronics, an on-off switch 20 and a battery, which housing is operatively connected to a transducer 1, cochlear electrode array 79, and a microphone housing 21 via connector cables 25, 82, and 24 respectively. The base of the transducer 1 is preferably coated with a compliant material, such as silicone, to create an impedance mismatched barrier to the transfer of vibrational energy from the base into bone surrounding the compliant material. Such arrangement assists to direct the transducer vibrations preferentially to the portion of the transducer 1 that is osseointegrated in the bone surrounding the otic capsule. Similarly, for reasons described in FIG. 2, the microphone housing 21 is preferably encapsulated in a compliant material, such as silicone, such encapsulation creating an acoustic impedance between the microphone housing 21 and the surrounding bone. RF coil 22 is used for transcutaneous communication between a similar external coil for battery charging and monitoring functions with the electronics in the main housing 19. A magnet 26 is located within the coil 22 to help align the internal RF coil 22 with an external coil (not shown) used to communicate with the internal coil 22. A cochlear electrode array 79, which devices are well documented by prior art, can be used simultaneously in conjunction with the transducer 1, in order to provide combined electrical and acoustic stimulation to the implantee. The electrode array 79, preferably not inserted beyond the first cochlear turn in order to minimize surgical trauma of more apical regions, preferentially stimulates spiral ganglion cells within the cochlear basal region, which stimulation provides for high frequency hearing percepts. The transducer 1 is preferably tuned to provide low frequency stimulation to the remaining functional hair cells within the apical turns of the cochlea. The totally implantable prosthesis 75 could then be used by individuals with significant low frequency hearing and severe to profound high frequency hearing loss.

While the above is a complete description of preferred embodiments of the invention, various alternatives, modifications and equivalents may be used. It should be evident that the present invention is equally applicable by making appropriate modification to the embodiments described above. Therefore, the above description should not be taken as limiting the scope of the invention.

What is claimed is:

1. An implantable hearing device comprising:
   a cylindrical hermetic housing having one or more grooves that aid osseointegration and at least partially coated with a compliant material that increases impedance to acoustic waves between said cylindrical hermetic housing and surrounding bone and tissue;
   a vibrational assembly enclosed inside said cylindrical hermetic housing and having a controllable vibrating element and an inertial mass, wherein said inertial mass vibrates in response to vibration of said vibrating element; and
   an acoustic input mechanism operably linked to said vibrational assembly via a bioinert cable and having at least one microphone enclosed in a hermetic housing.

2. The hearing device of claim 1, wherein said microphone is configured to be implanted in the posterior wall of the external auditory canal.

3. The hearing device of claim 2, wherein said microphone is configured to be implanted substantially behind and above the auricle.

4. The hearing device of claim 2, wherein said microphone is configured to be implanted substantially near the cymba concha of the auricle.

* * * * *